(12) United States Patent
Kamee

(10) Patent No.: US 11,147,438 B2
(45) Date of Patent: Oct. 19, 2021

(54) ENDOSCOPE APPARATUS

(71) Applicant: OLYMPUS CORPORATION, Tokyo (JP)

(72) Inventor: Hiroyuki Kamee, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 730 days.

(21) Appl. No.: 15/920,526

(22) Filed: Mar. 14, 2018

(65) Prior Publication Data

US 2018/0199803 A1    Jul. 19, 2018

Related U.S. Application Data

(63) Continuation of application No. PCT/JP2015/076070, filed on Sep. 14, 2015.

(51) Int. Cl.
*A61B 1/06* (2006.01)
*A61B 1/045* (2006.01)
(Continued)

(52) U.S. Cl.
CPC ........ *A61B 1/0638* (2013.01); *A61B 1/00009* (2013.01); *A61B 1/045* (2013.01);
(Continued)

(58) Field of Classification Search
CPC .................................................. A61B 1/0638
See application file for complete search history.

(56) References Cited

U.S. PATENT DOCUMENTS

2008/0097173 A1*  4/2008  Soyemi .............. A61B 5/14551
                                                     600/310
2011/0237883 A1*  9/2011  Chun ................... A61B 1/0638
                                                     600/109
(Continued)

FOREIGN PATENT DOCUMENTS

JP     H10-286235 A     10/1998
JP     2001-137172 A    5/2001
(Continued)

OTHER PUBLICATIONS

English translation of International Preliminary Report on Patentability dated Mar. 29, 2018 together with the Written Opinion received in related International Application No. PCT/JP2015/076070.
(Continued)

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

An endoscope apparatus includes an illumination apparatus that applies first and second narrow-band light having different peak wavelengths to a subject, an imaging device that acquires image light from the subject with pixels to generate an acquisition image signal, and an image processing circuit. The image processing circuit includes a storage that has stored assumed subject types including information about a wavelength range of assumed subjects, and a subject type decision circuit that decides an assumed subject type for part of the pixels based on a first image signal about the first narrow-band light, a second image signal about the second narrow-band light, and the assumed subject types. The image processing circuit constructs a display image signal based on the acquisition image signal and decided assumed subject type.

12 Claims, 13 Drawing Sheets

(51) Int. Cl.
*A61B 1/00* (2006.01)
*A61B 1/05* (2006.01)
*A61B 1/07* (2006.01)
*A61B 5/1455* (2006.01)

(52) U.S. Cl.
CPC ............... *A61B 1/05* (2013.01); *A61B 1/063* (2013.01); *A61B 1/0669* (2013.01); *A61B 1/07* (2013.01); *A61B 5/14551* (2013.01)

(56) References Cited

U.S. PATENT DOCUMENTS

2012/0053434 A1 3/2012 Saito
2012/0177259 A1 7/2012 Hirota et al.
2012/0327205 A1 12/2012 Takahashi
2014/0316195 A1 10/2014 Kaku et al.

FOREIGN PATENT DOCUMENTS

| | | |
|---|---|---|
| JP | 2011-135983 A | 7/2011 |
| JP | 2011-194082 A | 10/2011 |
| JP | 2012-066066 A | 4/2012 |
| JP | 2012-070839 A | 4/2012 |
| JP | 2012-143340 A | 8/2012 |
| JP | 2012-152333 A | 8/2012 |
| JP | 2013-150712 A | 8/2013 |

OTHER PUBLICATIONS

Japanese Office Action dated Feb. 26, 2019 in Japanese Patent Application No. 2017-540365.
International Search Report dated Dec. 8, 2015 issued in PCT/JP2015/076070.

\* cited by examiner

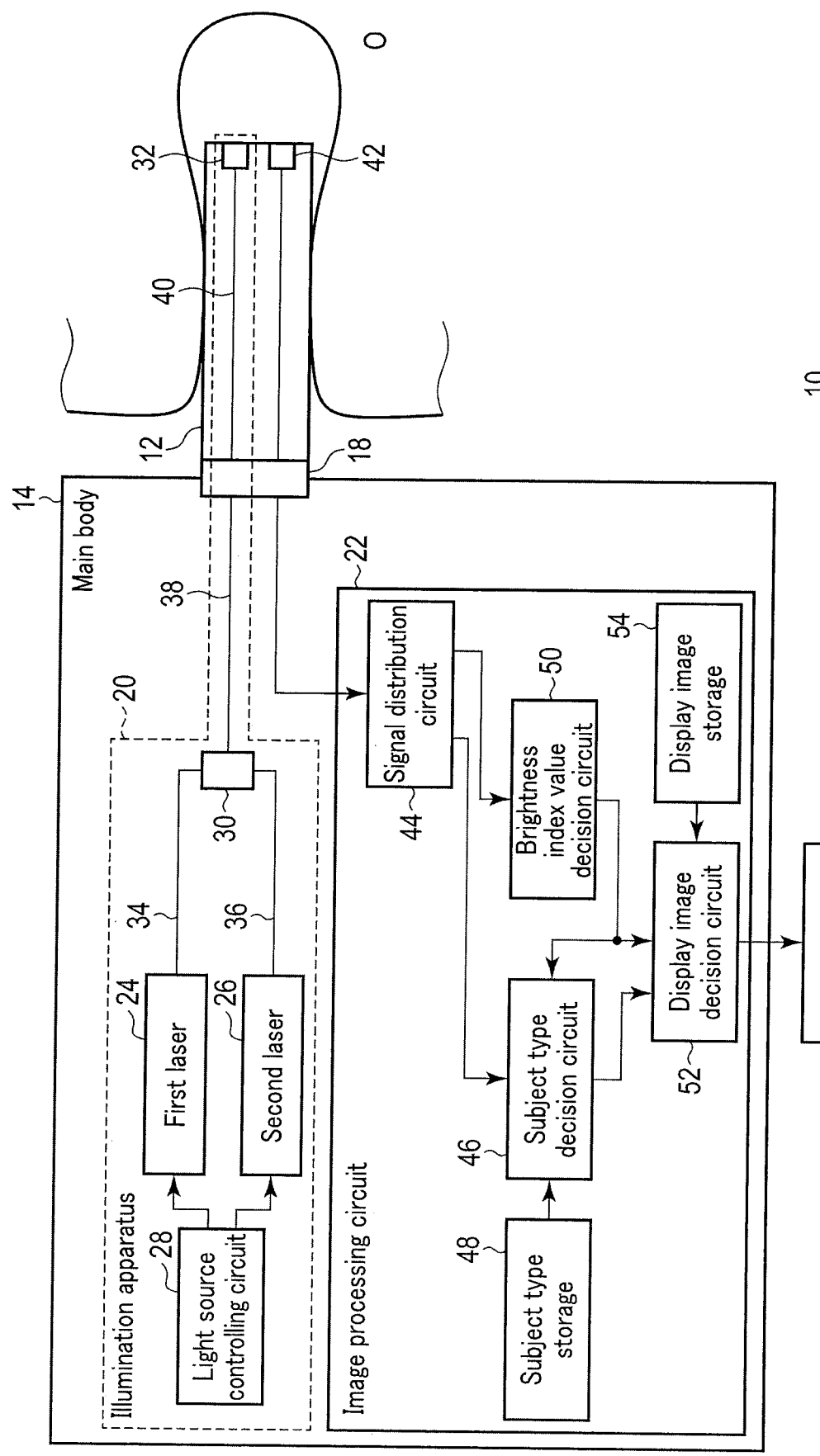
F I G. 1

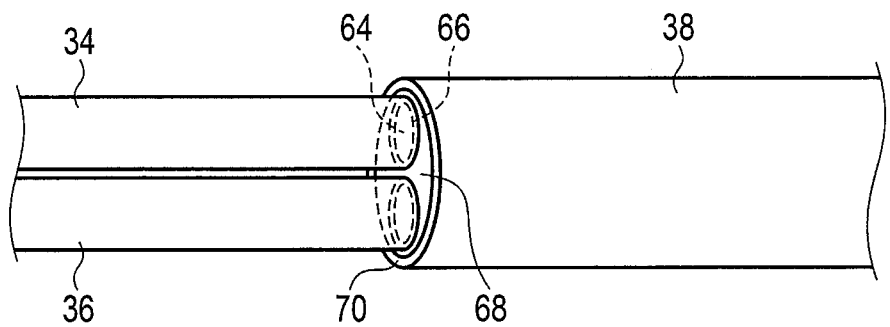
F I G. 4
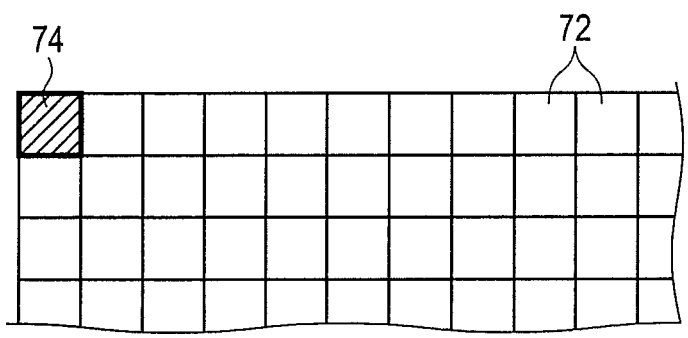
F I G. 5A
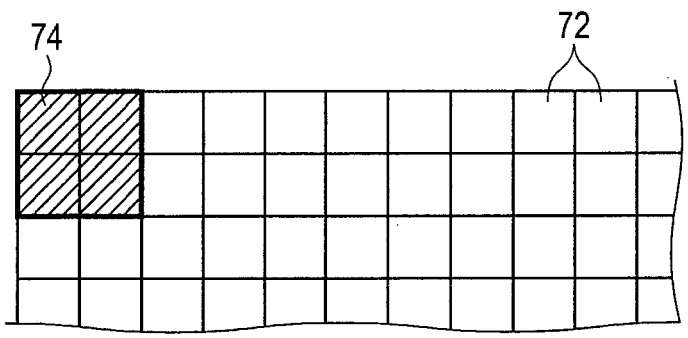
F I G. 5B

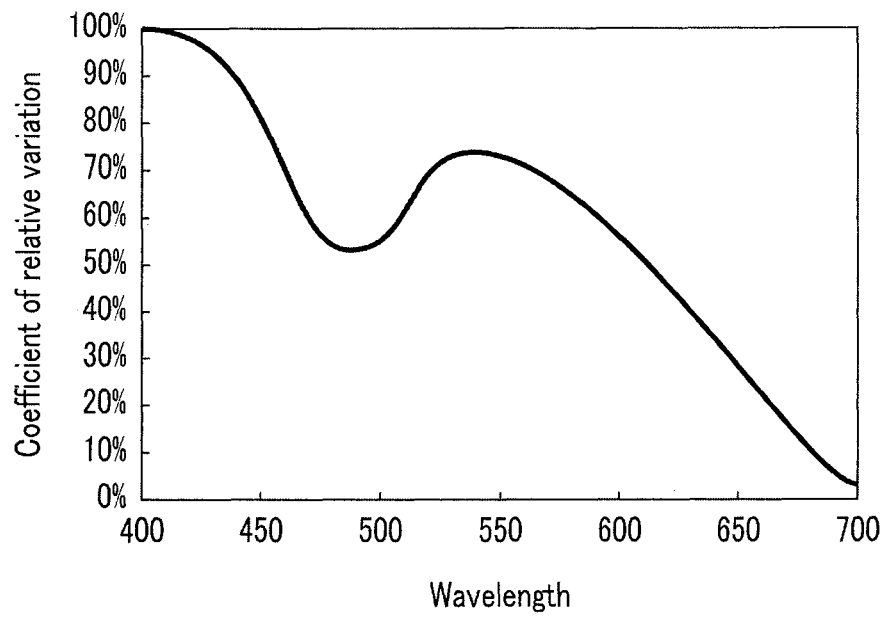
F I G. 10
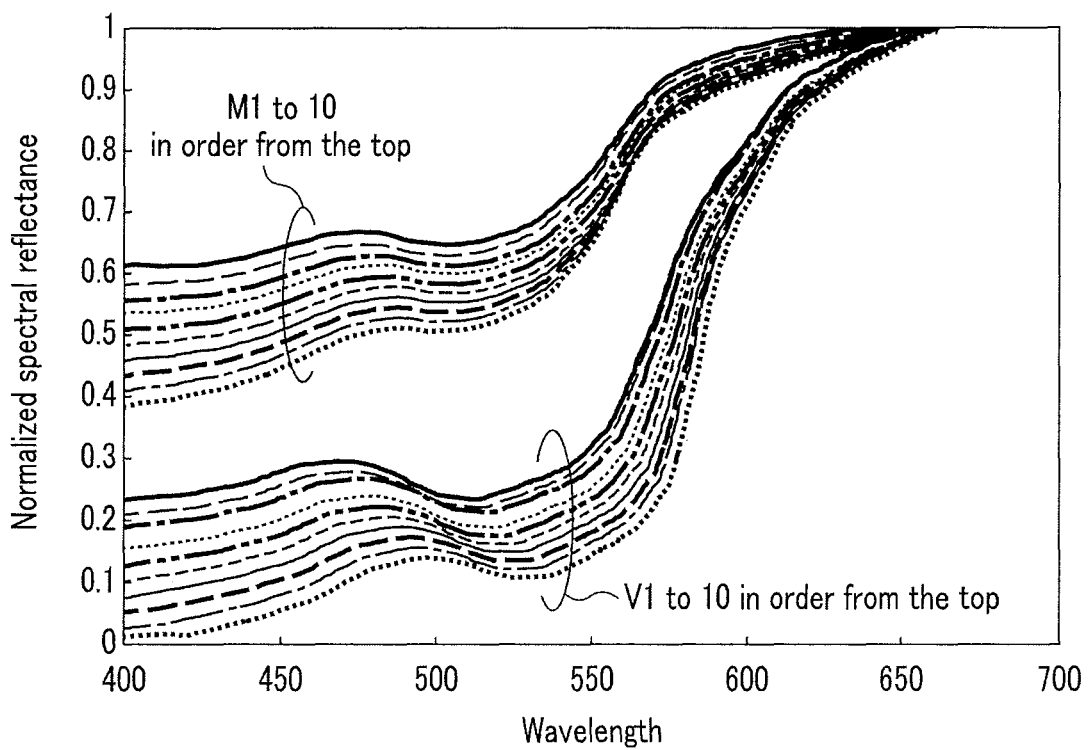
F I G. 11

| 405 nm/660 nm signal value | Subject type number |
|---|---|
| 0.64 or more and less than 0.66 | M1 |
| 0.62 or more and less than 0.64 | M2 |
| 0.58 or more and less than 0.62 | M3 |
| 0.56 or more and less than 0.58 | M4 |
| 0.51 or more and less than 0.56 | M5 |
| 0.48 or more and less than 0.51 | M6 |
| 0.44 or more and less than 0.48 | M7 |
| 0.41 or more and less than 0.44 | M8 |
| 0.38 or more and less than 0.41 | M9 |
| 0.36 or more and less than 0.38 | M10 |
| 0.20 or more and less than 0.22 | V1 |
| 0.18 or more and less than 0.20 | V2 |
| 0.15 or more and less than 0.18 | V3 |
| 0.13 or more and less than 0.15 | V4 |
| 0.10 or more and less than 0.13 | V5 |
| 0.08 or more and less than 0.10 | V6 |
| 0.06 or more and less than 0.08 | V7 |
| 0.04 or more and less than 0.06 | V8 |
| 0.02 or more and less than 0.04 | V9 |
| 0 or more and less than 0.02 | V10 |

FIG. 12

| Type of subject \ Brightness | 0 | 1 | 2 | ... | 4095 |
|---|---|---|---|---|---|
| M1 | R=0, G=0, B=0 | R=1, G=1, B=1 | R=2, G=2, B=1 | ... | R=4055, G=3379, B=2867 |
| M2 | R=0, G=0, B=0 | R=1, G=1, B=1 | R=2, G=2, B=1 | ... | R=4046, G=3370, B=2662 |
| M3 | R=0, G=0, B=0 | R=1, G=1, B=1 | R=2, G=2, B=1 | ... | R=4038, G=3320, B=2458 |
| M4 | R=0, G=0, B=0 | R=1, G=1, B=1 | R=2, G=2, B=1 | ... | R=4029, G=3277, B=2376 |
| M5 | R=0, G=0, B=0 | R=1, G=1, B=1 | R=2, G=2, B=1 | ... | R=4021, G=3236, B=2253 |
| M6 | R=0, G=0, B=0 | R=1, G=1, B=1 | R=2, G=2, B=1 | ... | R=4012, G=3072, B=2130 |
| M7 | R=0, G=0, B=0 | R=1, G=1, B=1 | R=2, G=2, B=1 | ... | R=4003, G=3031, B=2048 |
| M8 | R=0, G=0, B=0 | R=1, G=1, B=0 | R=2, G=1, B=1 | ... | R=3995, G=2926, B=1966 |
| M9 | R=0, G=0, B=0 | R=1, G=1, B=0 | R=2, G=1, B=1 | ... | R=3986, G=2908, B=1925 |
| M10 | R=0, G=0, B=0 | R=1, G=1, B=0 | R=2, G=1, B=1 | ... | R=3978, G=2867, B=1843 |
| V1 | R=0, G=0, B=0 | R=1, G=1, B=0 | R=2, G=1, B=1 | ... | R=3969, G=2853, B=1024 |
| V2 | R=0, G=0, B=0 | R=1, G=1, B=0 | R=2, G=1, B=0 | ... | R=3960, G=2763, B=922 |
| V3 | R=0, G=0, B=0 | R=1, G=1, B=0 | R=2, G=1, B=0 | ... | R=3943, G=2662, B=819 |
| V4 | R=0, G=0, B=0 | R=1, G=1, B=0 | R=2, G=1, B=0 | ... | R=3935, G=2458, B=717 |
| V5 | R=0, G=0, B=0 | R=1, G=1, B=0 | R=2, G=1, B=0 | ... | R=3926, G=2253, B=614 |
| V6 | R=0, G=0, B=0 | R=1, G=1, B=0 | R=2, G=1, B=0 | ... | R=3917, G=2048, B=512 |
| V7 | R=0, G=0, B=0 | R=1, G=0, B=0 | R=2, G=1, B=0 | ... | R=3909, G=1843, B=410 |
| V8 | R=0, G=0, B=0 | R=1, G=0, B=0 | R=2, G=1, B=0 | ... | R=3900, G=1638, B=307 |
| V9 | R=0, G=0, B=0 | R=1, G=0, B=0 | R=2, G=1, B=0 | ... | R=3891, G=1229, B=205 |
| V10 | R=0, G=0, B=0 | R=1, G=0, B=0 | R=2, G=0, B=0 | ... | R=3890, G=819, B=201 |

FIG. 13

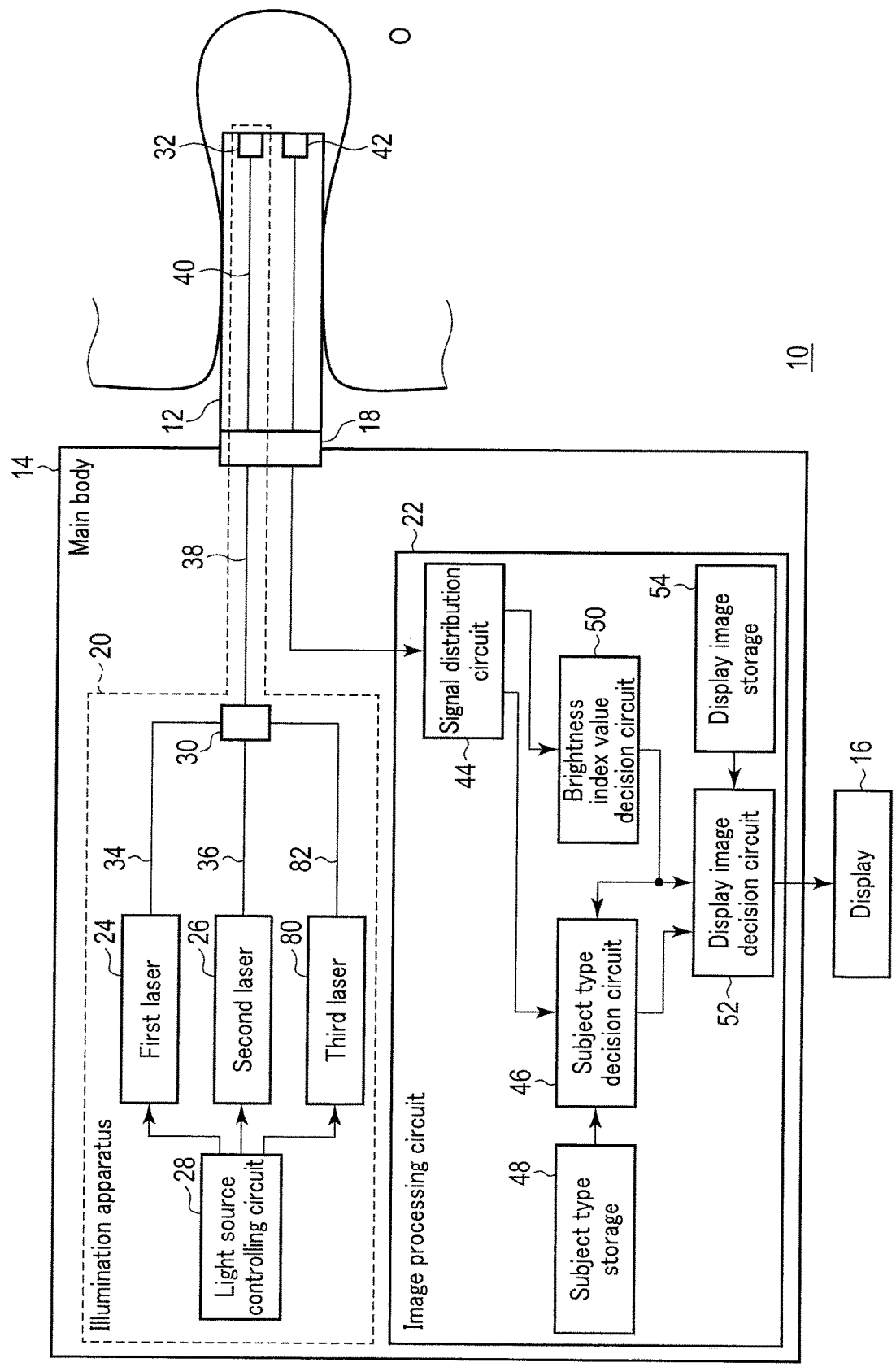
F I G. 15

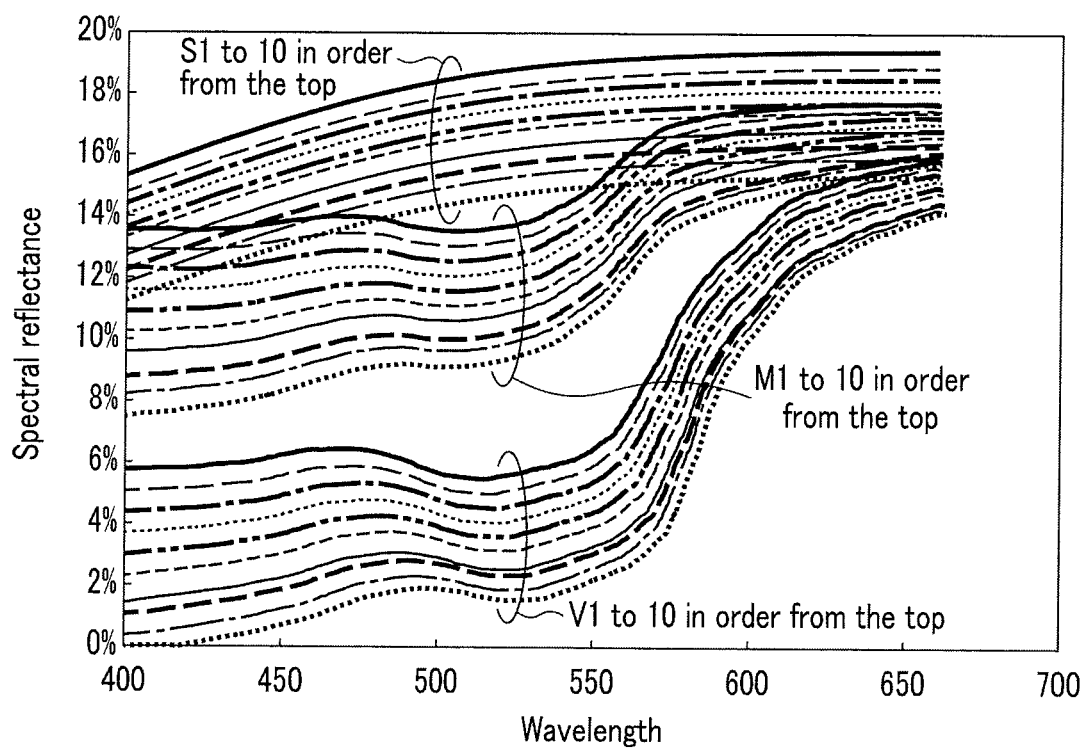
F I G. 16
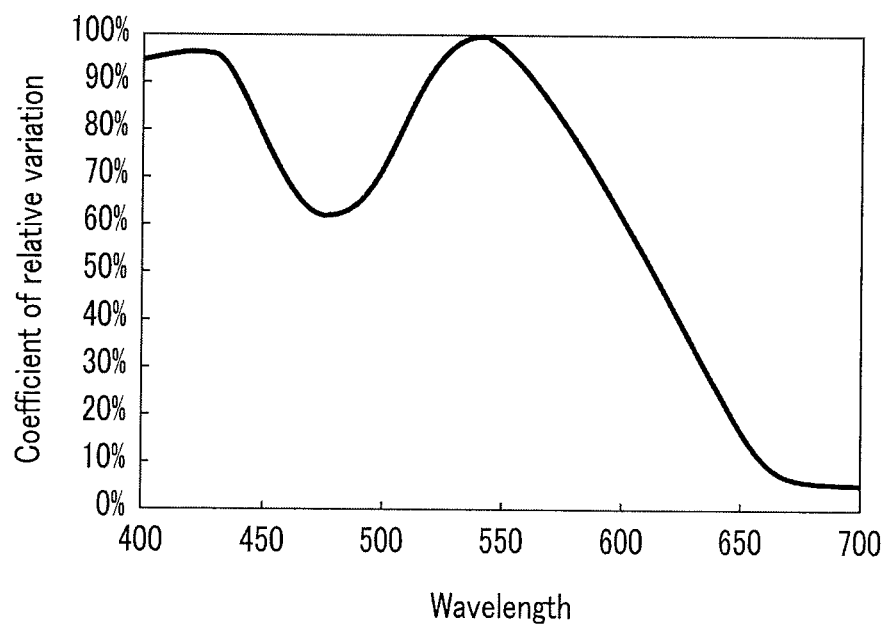
F I G. 17

| 405 nm/660 nm signal value \ 530 nm/660 nm signal value | 0 or more and less than 0.4 | 0.4 or more and less than 0.6 | 0.6 or more and less than 0.7 | 0.7 or more and less than 0.9 | 0.9 or more and less than 0.95 | 0.95 or more and less than 1.0 | 1.0 or more |
|---|---|---|---|---|---|---|---|
| 0.66 or more | E1 | E1 | E1 | E1 | E1 | E1 | E1 |
| 0.64 or more and less than 0.66 | E1 | E1 | E1 | M1 | E1 | S1 | E1 |
| 0.62 or more and less than 0.64 | E1 | E1 | E1 | M2 | E1 | S2 | E1 |
| 0.58 or more and less than 0.62 | E1 | E1 | E1 | M3 | E1 | S3 | E1 |
| 0.56 or more and less than 0.58 | E1 | E1 | E1 | M4 | E1 | S4 | E1 |
| 0.51 or more and less than 0.56 | E1 | E1 | E1 | M5 | E1 | S5 | E1 |
| 0.48 or more and less than 0.51 | E1 | E1 | E1 | M6 | E1 | S6 | E1 |
| 0.44 or more and less than 0.48 | E1 | E1 | E1 | M7 | E1 | S7 | E1 |
| 0.41 or more and less than 0.44 | E1 | E1 | E1 | M8 | E1 | S8 | E1 |
| 0.38 or more and less than 0.41 | E1 | E1 | E1 | M9 | E1 | S9 | E1 |
| 0.36 or more and less than 0.38 | E1 | E1 | E1 | M10 | E1 | S10 | E1 |
| 0.20 or more and less than 0.22 | E1 | V1 | E1 | E1 | E1 | E1 | E1 |
| 0.18 or more and less than 0.20 | E1 | V2 | E1 | E1 | E1 | E1 | E1 |
| 0.15 or more and less than 0.18 | E1 | V3 | E1 | E1 | E1 | E1 | E1 |
| 0.13 or more and less than 0.15 | E1 | V4 | E1 | E1 | E1 | E1 | E1 |
| 0.10 or more and less than 0.13 | E1 | V5 | E1 | E1 | E1 | E1 | E1 |
| 0.08 or more and less than 0.10 | E1 | V6 | E1 | E1 | E1 | E1 | E1 |
| 0.06 or more and less than 0.08 | E1 | V7 | E1 | E1 | E1 | E1 | E1 |
| 0.04 or more and less than 0.06 | E1 | V8 | E1 | E1 | E1 | E1 | E1 |
| 0.02 or more and less than 0.04 | E1 | V9 | E1 | E1 | E1 | E1 | E1 |
| 0 or more and less than 0.02 | E1 | V10 | E1 | E1 | E1 | E1 | E1 |

FIG. 20

ENDOSCOPE APPARATUS

CROSS REFERENCE TO RELATED APPLICATIONS

This application is a Continuation Application of PCT Application No. PCT/JP2015/076070, filed Sep. 14, 2015, the entire contents of which are incorporated herein by reference.

BACKGROUND OF THE INVENTION

1. Field of the Invention

The present invention relates to an endoscope apparatus.

2. Description of the Related Art

Currently, what is called a fiber light source device in which a small-sized light source and an optical fiber are combined is developed. The fiber light source device is particularly suitable to be used as a light source device that emits illumination light from the distal end of a thin structure.

For example, Jpn. Pat. Appln. KOKAI Publication No. 10-286235 discloses a fiber light source device in which a laser light source that emits laser light of three RGB colors simultaneously, an optical fiber, and a diffusion plate are combined. Jpn. Pat. Appln. KOKAI Publication No. 10-286235 proposes equipping an endoscope apparatus with the fiber light source device. Since the light source device in which a three-RGB-color laser light source, an optical fiber, and a diffusion plate are combined is very increased in efficiency of guiding laser light to the diffusion plate, it is attracting attention as a technology capable of emitting bright light with high efficiency.

The fiber light source device disclosed in Jpn. Pat. Appln. KOKAI Publication No. 10-286235 employs an He—Cd second laser that is a three-primary-color (white-color) laser that oscillates blue laser light of 441.6 nm, green laser light of 537.8 nm, and red laser light of 636.0 nm simultaneously. The three-primary-color (white-color) laser light emitted from the He—Cd second laser is guided to the distal end section of an endoscope by a light guide and then applied to a living body that is an illumination target object, through the diffusion plate and a luminance distribution adjustment filter.

In general, when laser light is diffused and used as illumination light, the problem is lack of information about light with wavelengths not included the laser light. More specifically, it is known that color reproducibility deteriorates when there is a difference in reflectance of a living body that is an illumination target object between red laser light of 636.0 nm oscillated by the He—Cd second laser and light with wavelengths close thereto, and light with the other wavelengths in a red range. For example, when the illumination target object hardly reflects light with wavelengths close to 636 nm but reflects the other light in the red range sufficiently, the problem is that even though the illumination target object actually appears red, it will appear dark if it is illuminated with laser light.

To prevent the above problems, Jpn. Pat. Appln. KOKAI Publication No. 10-286235 discloses that color reproducibility can be improved by the addition of red light of 632.8 nm and furthermore laser light with red wavelengths can be combined. More specifically, the fiber light source device disclosed in Jpn. Pat. Appln. KOKAI Publication No. 10-286235 is configured to combine white-color laser light emitted from the He—Cd second laser and red-color laser light emitted from an He—Ne second laser that emits light with a red wavelength of 632.8 nm by a beam splitter, guide the combined laser light to the distal end section of the endoscope by the light guide and apply the laser light to a living body that is an illumination target object, through the diffusion plate and the luminance distribution adjustment filter.

BRIEF SUMMARY OF THE INVENTION

An endoscope apparatus includes an illumination apparatus that applies first wavelength narrow-band light and second wavelength narrow-band light that have peak wavelengths different from each other to a subject, an imaging device that acquires image light from the subject with pixels to generate an acquisition image signal, and an image processing circuit that constructs a display image signal. The image processing circuit includes a storage that has stored assumed subject types including information about a wavelength range of assumed subjects, and a subject type decision circuit that decides an assumed subject type for part of the pixels based on a first wavelength image signal that is image light information about the first wavelength narrow-band light, a second wavelength image signal that is image light information about the second wavelength narrow-band light, the first and second wavelength image signals being included in the acquisition image signal, and the assumed subject types stored in the storage. The image processing circuit constructs the display image signal based on the acquisition image signal generated by the imaging device and the assumed subject type decided by the subject type decision circuit.

Additional objects and advantages of the invention will be set forth in the description that follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic block diagram showing a configuration of an endoscope apparatus according to a first embodiment of the present invention.

FIG. 4 is a perspective view illustrating a configuration of an optical fiber type combiner as an example of a combiner.

FIG. 5A is a chart showing an example of an assumed subject type decision unit for pixels of an imaging device.

FIG. 5B is a chart showing another example of the assumed subject type decision unit for the pixels of the imaging device.

FIG. 10 is a graph showing an example of a coefficient of relative variation at each wavelength for the subjects of subject type numbers M1 to M10 and V1 to V10.

FIG. 11 is a graph showing visible light spectral reflectance for each spectrum type normalized at 660 nm.

FIG. 12 is an example of a first data table stored in a subject type storage and representing the subject type numbers corresponding to assumed subject type index values (405 nm/660 nm signal values).

FIG. 13 is an example of a second data table stored in a display image storage and representing display image signal values corresponding to the subject type numbers and brightness index values.

FIG. 15 is a schematic block diagram showing a configuration of an endoscope apparatus according to a second embodiment of the present invention.

FIG. 16 is a graph showing an example of spectral reflectance spectra of subjects of subject type numbers M1 to M10, V1 to V10 and S1 to S10.

FIG. 17 is a graph showing an example of a coefficient of relative variation at the wavelength for each of the subjects of subject type numbers M1 to M10, V1 to V10 and S1 to S10.

FIG. 20 is an example of a third data table stored in a subject type storage and representing the subject type numbers corresponding to first assumed subject type index values (405 nm/660 nm signal values) and second assumed subject type index values (530 nm/660 nm signal values).

DETAILED DESCRIPTION OF THE INVENTION

Figure 2:
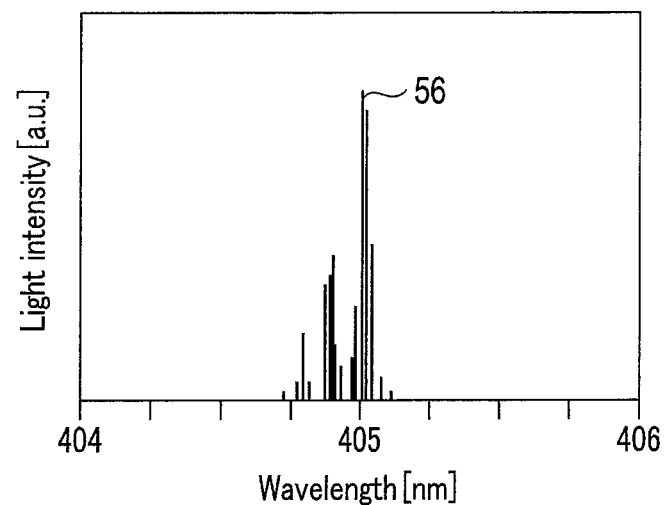
FIG. 2 is a graph showing an example of an emission spectrum of a first laser that emits laser light with a peak wavelength of 405 nm.

Embodiments of the present invention will be described below with reference to the drawings.

First Embodiment

The endoscope apparatus 10 according to the first embodiment is a medical endoscope apparatus in which the body of human beings or animals is assumed as a subject O.

As shown in FIG. 1, in order to observe a subject O that is an observation target object in the body of human beings or animals, the endoscope apparatus 10 includes an insertion section 12 to be inserted into the body, a main body 14 including a light source and an image construction function, and a display 16 that displays an image of the subject O. The insertion section 12 is freely detachable from the main body 14 through a connector 1.

The main body 14 includes a part of an illumination apparatus 20 and an image processing circuit 22. The insertion section 12 includes the other part of the illumination apparatus 20. In other words, the endoscope apparatus 10 includes the illumination apparatus 20, which applies illumination light to the subject O that is an observation target object in the body of human beings or animals, and the structural members of the illumination apparatus 20 are assigned to the insertion section 12 and the main body 14.

The main body 14 further includes an input device to receive various instructions from an operator and a controller to control each portion of the endoscope apparatus 10 according to the instructions provided through the input device, though not shown in particular.

Specifically, the illumination apparatus 20 includes a first laser 24, a second laser 26, a light source controlling circuit 28, a combiner 30, a light radiating portion 32, and optical fibers 34, 36, 38, and 40. The first laser 24, second laser 26, light source controlling circuit 28, combiner 30, and optical fibers 34, 36, and 38 are arranged in the main body 14, and the light radiating portion 32 and optical fiber 40 are arranged in the insertion section 12. This arrangement is, however, an example, and the present invention is not limited to the arrangement.

The first and second lasers 24 and 26 are semiconductor lasers whose emission light wavelengths are different from each other. The light source controlling circuit 28 controls the quantity of laser light emitted from each of the first and second lasers 24 and 26, turn-on/turn-off of each laser, and the like. The laser light emitted from the first laser 24 is guided by the optical fiber 34 and the laser light emitted from the second laser 26 is guided by the optical fiber 36. The combiner 30 combines the laser light guided from the first and second lasers 24 and 26 by the optical fibers 34 and 36 and causes the combined laser light to enter the optical fiber 38. The optical fiber 38, which guides the laser light emitted from the first and second lasers 24 and 26 and combined by the combiner 30, is optically connected to the optical fiber 40 in the insertion section 12 through an optical connector (not shown) provided in the connector 18. Accordingly, the laser light guided through the optical fiber 38 from the first and second lasers 24 and 26 enters the optical fiber 40 and is guided to the light radiating portion 32 disposed at the distal end section of the insertion section 12. The light radiating portion 32 appropriately converts the laser light guided by the optical fiber 40 into light with characteristics suitable for illumination and radiates it to the front of the insertion section 12.

The distal end section of the insertion section 12 is also provided with an imaging element 42 that is an imaging device that acquires image light from the subject O with pixels to generate an acquisition image signal. A signal line that transmits an electrical signal of information of the image light acquired by the imaging element 42 extends from the imaging element 42 to the main body 14 through the insertion section 12. Thus, the imaging element 42 is electrically connected to the image processing circuit 22 in the main body 14 through the connector 18.

The image processing circuit 22 constructs a display image signal to be displayed on the display 16 based on an image signal acquired by the imaging element 42 that is an imaging device. The image processing circuit 22 includes a signal distribution circuit 44, a subject type decision circuit 46, a subject type storage 48, a brightness index value decision circuit 50, a display image decision circuit 52, and a display image storage 54. Note that the signal distribution circuit 44, subject type decision circuit 46, brightness index value decision circuit 50, and display image decision circuit 52 can be configured by hardware and constructed by software executed by a processor such as a CPU. The subject type storage 48 and display image storage 54 can be configured by a semiconductor memory, a magnetic disk, and the like. The operations of these circuits and storages will be described in detail later. The image processing circuit 22 decides a subject type and brightness for each pixel or for each set of pixels from the acquired image signal, decides a display image signal in which the color of the subject O is reproduced based on the information, and transmits it to the display 16.

The display 16 displays the display image signal transmitted from the image processing circuit 22.

The insertion section 12 has an elongated, cylindrical appearance to be easily inserted into the internal space of human beings or animals. As the subject O, for example, a slightly expanded inner wall that exists in the back of a narrow entrance can be considered as shown in FIG. 1. External light such as indoor illumination and solar light hardly enters the subject O. If the insertion section 12 is particularly inserted into the entrance, it will block the entrance that is originally narrow, and consequently almost no external light enters the inside. In other words, most of the illumination light into the subject O of the internal space is only the illumination light radiated from the light radiating portion 32. As compared with the illumination light, the external light can be almost ignored. The endoscope apparatus 10 according to the first embodiment is suitable to observe the internal space in which external light can be almost ignored as compared with illumination light.

The configuration and operation of each portion will be described further in detail below.

<First and Second Lasers 24 and 26>

A semiconductor laser is a solid-state light source device that causes current to flow through a semiconductor element to emit laser light. The semiconductor laser has the advantages of decreasing in size, saving power, and the like and has recently actively developed toward high luminance and wavelength diversification. Laser light is generally narrow-band light having wavelength characteristics of a line spectrum whose wavelength width is very narrow. In the semiconductor laser, generally, the width of a spectrum line (spectrum line width) is 1 nm or less.

The illumination apparatus 20 of the endoscope apparatus 10 according to the first embodiment includes two semiconductor lasers of the first and second lasers 24 and 26, the emission wavelength of the former is shorter than that of the latter. Specifically, the first laser 24 is a multimode semiconductor laser that emits blue-violet laser light with a wavelength of approximately 405 nm (first wavelength narrow-band light), and the second laser 26 is a multimode semiconductor laser that emits red laser light with a wavelength of approximately 660 nm (second wavelength narrow-band light).

Each semiconductor laser is a multimode laser and emits laser with wavelengths as shown in, e.g. FIG. 2. The emission wavelengths including the shortest one to the longest one fall within a wavelength range of 1 nm or less. FIG. 2 shows an example of an emission spectrum of the first laser 24 that emits laser with a peak wavelength 56 of 405 nm.

The emission spectrum contains several tens of line spectrum components, and the ratio and the number of line spectra vary with time. The width of the wavelength range of the emission spectrum is approximately 1 nm. When multimode laser light having such a spectrum is used as arrow-band light, the peak wavelength 56 of the narrow-band light is defined as a wavelength ($\lambda$peak) corresponding to the highest light intensity. In the first embodiment, the peak wavelength 56 of the first laser 24 is 405 nm (=$\lambda$peak). The peak wavelength of the second laser 26 is 660 nm (=$\lambda$peak).

Figure 3:
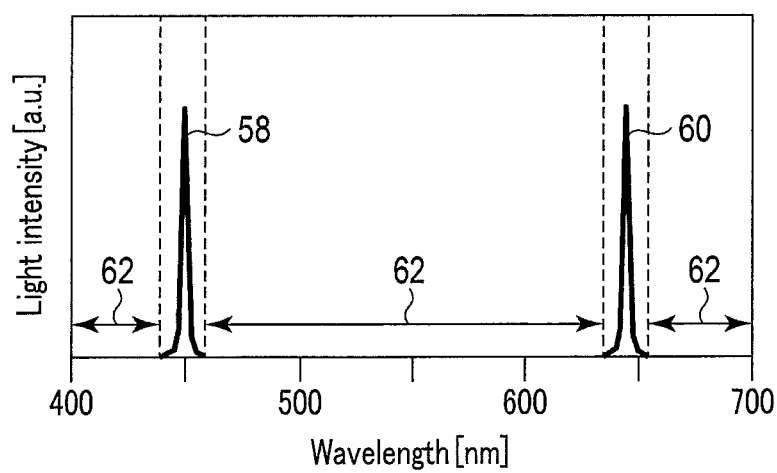
FIG. 3 is a graph illustrating a missing range.

As shown in FIG. 3, in a range between two laser light spectra 58 and 60 that are adjacent to each other in terms of wavelength, a range with almost no laser light is defined as a wavelength missing range 62. More specifically, a range whose intensity is $1/100$ lower than the highest peak intensity of laser light is defined as the wavelength missing range 62.

<Light Source Controlling Circuit 28>

The light source controlling circuit 28 has a function capable of controlling the first and second lasers 24 and 26 alone or in association with each other.

If the light source controlling circuit 28 controls the first and second lasers 24 and 26 to increase and decrease the total quantity of light with a fixed ratio of quantity of light of the first and second lasers 24 and 26, only the brightness can be increased and decreased without varying the color of illumination light. Also, the light source controlling circuit 28 can adjust the quantities of light of the first and second lasers 24 and 26 individually and vary the color of illumination light. Furthermore, if the light source controlling circuit 28 controls all the lasers to blink simultaneously, an illumination apparatus 20 in which the lasers blink at a desired color is constructed. Also, if the light source controlling circuit 28 blinks the first and second lasers 24 and 26 in sequence at different times, an illumination apparatus 20 in which the color of illumination light varies successively is constructed.

The light source controlling circuit 28 can be configured to perform other different control operations depending on their intended use. Note that the light source controlling circuit 28 can be configured by hardware and constructed by software executed by a processor such as a CPU.

In the first embodiment, the light source controlling circuit 28 controls lighting so that the above laser light of two wavelengths are alternately radiated from the light radiating portion 32 to the first and second lasers 24 and 26 with timing when the imaging element 42 is appropriately exposed.

<Optical Fibers 34, 36, 38, and 40>

In the first embodiment, the optical fibers 34, 36, 38, and 40 are used to guide the laser light from the laser light sources to the combiner 30 or to guide the laser light from the combiner 30 to the light radiating portion 32. As the combiner 30, an optical fiber type combiner is used as will be described later.

As the optical fibers 34, 36, 38, and 40, various optical fibers that have been put to practical use can be used. Since, in the first embodiment, a multimode semiconductor laser is used as the laser, a multimode optical fiber is used to enter and guide multimode laser light with efficiency.

The optical fiber 34 includes a core 64 and its surrounding clad 66, as shown in FIG. 4. The same holds true for the optical fiber 36. The optical fiber 38, which has the diameter larger than that of each of the optical fibers 34 and 36, includes a core 68 and its surrounding clad 70. As the multimode optical fiber, an optical fiber whose core diameter is about several tens of μm to 200 μm is generally used.

The optical fiber 40, which is included in the insertion section 12 to guide laser light to the light radiating portion 32, includes a core and its surrounding clad, though not shown in particular. In the first embodiment, the optical fiber 40 has a core diameter of 50 μm, a clad diameter of 125 μm, and an NA of 0.2.

<Combiner 30>

The combiner 30 is an optical element having a function of combining light input upon input ends into light to be output from an output end. A combiner capable of coupling laser light from lasers to a single optical fiber, such as a space optical system combiner in which a cross prism, a dichroic mirror, etc. are combined and an optical fiber type combiner in which the core portions of optical fibers whose diameters are small are connected to the core portion of a single optical fiber whose diameter is large, can be used.

In the first embodiment, an optical fiber type combiner as shown in FIG. 4 is used as the combiner 30. FIG. 4 shows an example of a 2-in/1-out combiner in which two input-side optical fibers 34 and 36 connected to two input ports and an output-side optical fiber 38 connected to one output port are optically connected with their end faces opposed to and pushed on each other.

A multi-in/1-out combiner in which a number of input-side optical fibers are coupled to a single optical fiber as well as the 2-in/1-out combiner is put to practical use depending on the intended use. These different combiners 30 can thus be used.

If, furthermore, a 2×2 optical coupler in which the sides of cores of optical fibers are optically connected to each other is combined, light radiating portions 32 can be provided at the distal end section of the insertion section 12. Thus, even though the subject O has irregularities, a good observation image without shadow can be acquired. Moreover, various optical couplers, such as a 3×3 or more optical coupler, can be used alone or in combination with a combiner.

<Light Radiating Portion 32>

The light radiating portion 32 has a function of adjusting optical characteristics of laser light emitted from the two lasers 24 and 26 in accordance with illumination purpose and radiating it forward from the distal end section of the insertion section 12 as illumination light.

For example, the laser light guided through the optical fiber 40 travels in a very straight line and thus needs to be expanded at a radiation angle suitable for illumination light. The light radiating portion 32 has a function of adjusting a radiation angle and light distribution appropriately and radiating light forward with efficiency. To fulfill the function, the light radiating portion 32 can be configured using a transparent resin in which high-refractive-index particles such as alumina are dispersed or low-refractive-index structures such as fine bubbles are dispersed, ground glass having fine irregularities on its surface, and a complex of these materials. To make fine adjustments for the light distribution and radiation angle, an optical system such as a lens can be used. However, the light radiating portion 32 should not change the wavelength of laser light.

<Imaging Device>

The imaging device is configured by the imaging element 42 provided at the distal end section of the insertion section 12.

The endoscope apparatus 10 according to the first embodiment is based on the assumption that the insertion section 12 is inserted into the internal space of human beings or animals and the imaging element 42 is used in an environment capable of ignoring the quantity of external light such as natural light and indoor light as compared with the quantity of illumination light. The imaging element 42 thus acquires an image of the subject O in the internal space only by the reflection and scattering of illumination light radiated from the light radiating portion 32 toward the subject O. The imaging element 42 is a monochrome two-dimensional imaging element that includes pixels 72 arranged in rows and columns as shown in FIGS. 5A and 5B and does not have a color separation function of a color filter, etc. on the front of the pixels 72.

As described above, the light source controlling circuit 28 controls driving of the first and second lasers 24 and 26 so that blue-violet laser light with a wavelength of approximately 405 nm (first wavelength narrow-band light) and red laser light with a wavelength of approximately 660 nm (second wavelength narrow-band light) are radiated alternately from the light radiating portion 32. Thus, the imaging element 42 that is an imaging device selectively acquires a 405 nm image signal (first wavelength image signal) as image light information regarding the first wavelength narrow-band light in a state where the first wavelength narrow-band light is radiated. The imaging element 42 also selectively acquires a 660 nm image signal (second wavelength image signal) as image light information regarding the second wavelength narrow-band light in a state where the second wavelength narrow-band light is radiated.

Therefore, the imaging element 42 has a function of transmitting the selectively acquired first and second wavelength image signals in sequence to the main body 14.

<Signal Distribution Circuit 44>

The signal distribution circuit 44 transmits the acquired 405 nm image signal that is a first wavelength image signal to the subject type decision circuit 46 and transmits the acquired 660 nm image signal that is a second wavelength image signal to the brightness index value decision circuit 50.

When the signal distribution circuit 44 is configured by hardware, it can be configured by, for example, a changeover switch. The changeover switch switches a connection destination of a signal line from the imaging element 42 in such a manner that the signal line from the imaging element 42 is connected to a signal line to the subject type decision circuit 46 in synchronization with the driving of the first laser 24 and the signal line from the imaging element 42 is connected to a signal line to the brightness index value decision circuit 50 in synchronization with the driving of the second laser 26.

<Subject Type Memory 48>

The subject type storage 48 has stored assumed subject types that are assumed in advance as an observation target and an assumed subject type index value corresponding to each of the assumed subject types.

In observing a living body inner wall, such as an esophagus, a stomach, and the large intestine, from its inner surface, it is largely divided into two subject areas. One is a vascular area including blood vessels and the other is a mucosal area including no blood vessels.

Figure 6:
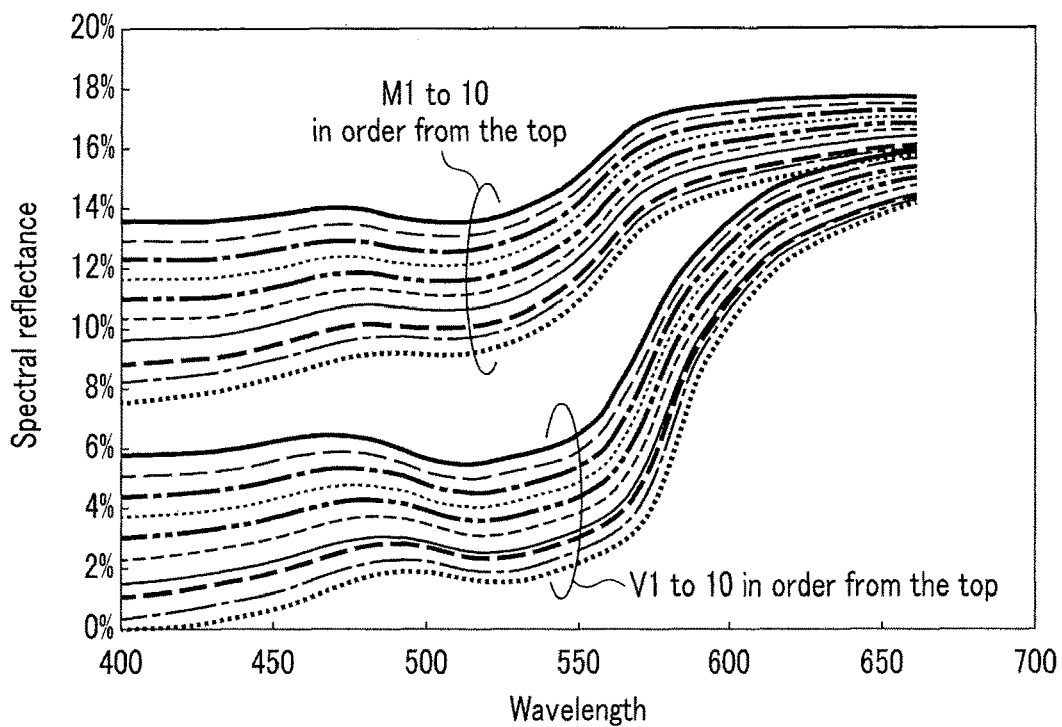
FIG. 6 is a graph showing an example of spectral reflectance spectra of subjects of subject type numbers M1 to M10 and V1 to V10.

FIG. 6 is a graph showing spectral reflectance spectra of various subjects O. In FIG. 6, subject type numbers M1 to M10 indicate a typical example of spectral reflectance spectra of a mucosal area, and subject type numbers V1 to V10 indicate a typical example of spectral reflectance spectra of a vascular area. The subjects O are all photographed at the same subject distance and at the same subject angle.

Of the subjects, inner wall spectrum information, such as all human being types (race, age, sex), all states (photograph time period, normal part, lesion part, cured part, treated part, etc.), and all areas (organs such as an esophagus, a stomach, and the large intestine, surface layer components such as mucus, residues, and bleeding blood), is stored in advance. For brevity, the number of subject types is limited to twenty in FIG. 6, but it is not limited thereto. The information should be stored on the assumption of all phenomena, scenes, and areas, and in this state a characteristic spectrum is extracted.

Figure 7:
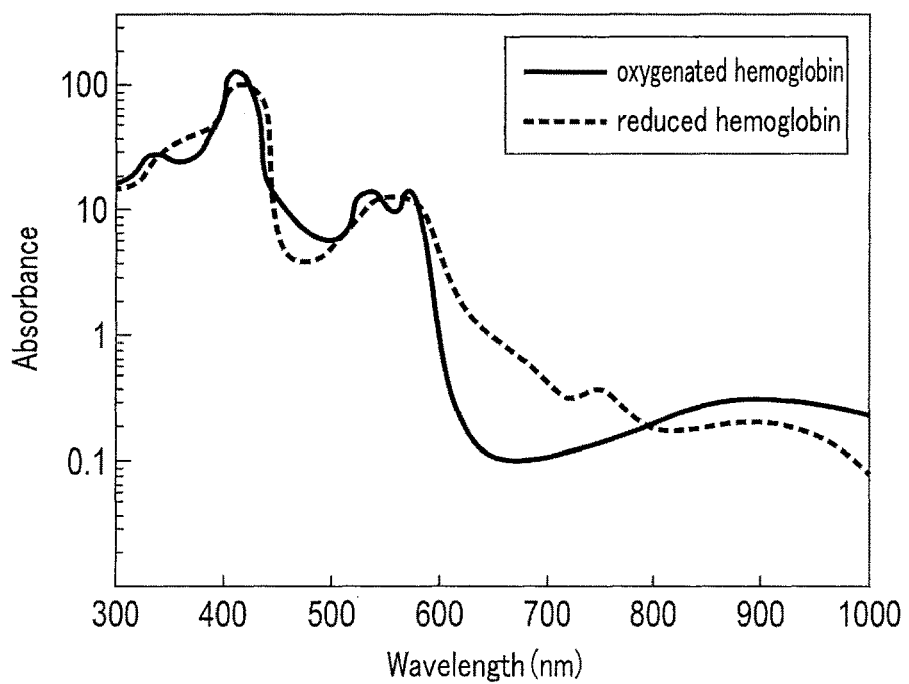
FIG. 7 is a graph showing spectral reflectance spectra of oxygenated hemoglobin and reduced hemoglobin.

The color taste of the living body inner wall is dominated by light absorption by hemoglobin regardless of the presence or absence of blood vessels, and most part of the living body inner wall is very reddish. FIG. 7 shows spectral reflectance spectra of oxygenated hemoglobin and reduced hemoglobin that are the principal absorbing dye of the living body inner wall.

To display an observation target limited as the subject O with high color reproducibility, only stable narrow spectral light whose wavelength can correctly be specified rather than a broad spectrum illumination light with good color rendering is applied to acquire detailed, correct subject spectral reflectance information regarding the wavelength. It is thus possible to specify the assumed subject type and brightness and construct an image with high color reproducibility.

Since the medical endoscope apparatus is particularly directed to closed space as an observation target, it hardly applies illumination light that is not assumed;

thus, it can acquire more detailed, more correct subject spectral reflectance information than a commonly-used endoscope apparatus.

Figure 8:
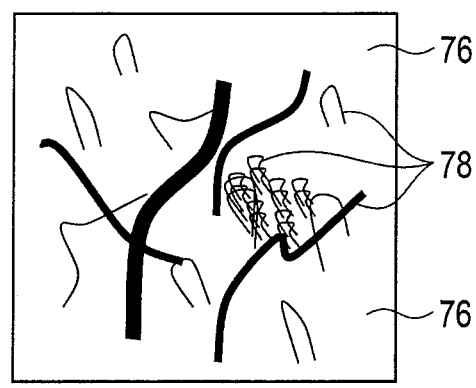
FIG. 8 is an illustration of a typical example of a displayed image of a living body inner wall.

FIG. 8 shows a typical example of a subject of the living body inner wall. The living body inner wall mainly includes a mucosal area 76 and a vascular area 78 as a type of subject O. In the mucosal area 76, the color taste slightly varies with the state of a plica, the shape of a mucous membrane, a difference between organ ranges, a difference between normal part and lesion part, etc. In the vascular area 78, similarly, the color taste varies with the thickness and depth of a blood vessel, a difference between a vein and an artery, a difference between organ ranges, a difference between normal part and lesion part, etc.

A subject image displayed as a color image is originally large and is formed by two items of a luminance signal (brightness) and a chromaticity signal (color taste). The main factor to decide the brightness varies with the distance of the subject O from the imaging element 42, a relative angle between the imaging surface of the imaging element 42 and the surface of the subject, the quantity of illumination to be applied, light distribution, imaging element spectral sensitivity characteristics, etc. The color taste also varies mainly with the type of subject O. If, therefore, the type and brightness of the subject O can correctly be grasped, a high reproducibility image can be displayed without applying illumination with good color rendering.

As shown in FIG. 7, the absorption of hemoglobin is dominant in the vicinity of a visible light wavelength. A wavelength range in which the absorbance is 10 or more, in which the acquired signal value greatly varies with the type of the subject, is in the vicinity of the range from 400 to 450 nm for both of the oxygenated hemoglobin and the reduced hemoglobin. Conversely, a wavelength range in which the absorbance is low and 1 or less, in which the variation of the acquired signal value can be almost ignored depending on the type of the subject, is 600 nm or more for the oxygenated hemoglobin and is 660 nm or more for the reduced hemoglobin. It is thus when the wavelength is 660 nm or more that both the oxygenated hemoglobin and reduced hemoglobin absorb almost no light. Therefore, when the living body inner wall is the subject O, the wavelength at which brightness can be specified without depending upon the type of the subject O is 660 nm or more. When illumination light in this wavelength range is applied to the living body inner wall, it is reflected from the living body relatively efficiently, which brings about the advantages that brightness can easily be recognized with a small quantity of light and information about brightness can correctly be obtained from a dark portion by decreasing driving power and adjusting quantity of light appropriately.

As for the color taste, to acquire the concentration of hemoglobin that is the principal dye minutely and correctly, a wavelength in a range from 400 nm to 450 nm at which the reflectance most greatly varies with the concentration of hemoglobin is desirable.

Figure 9:
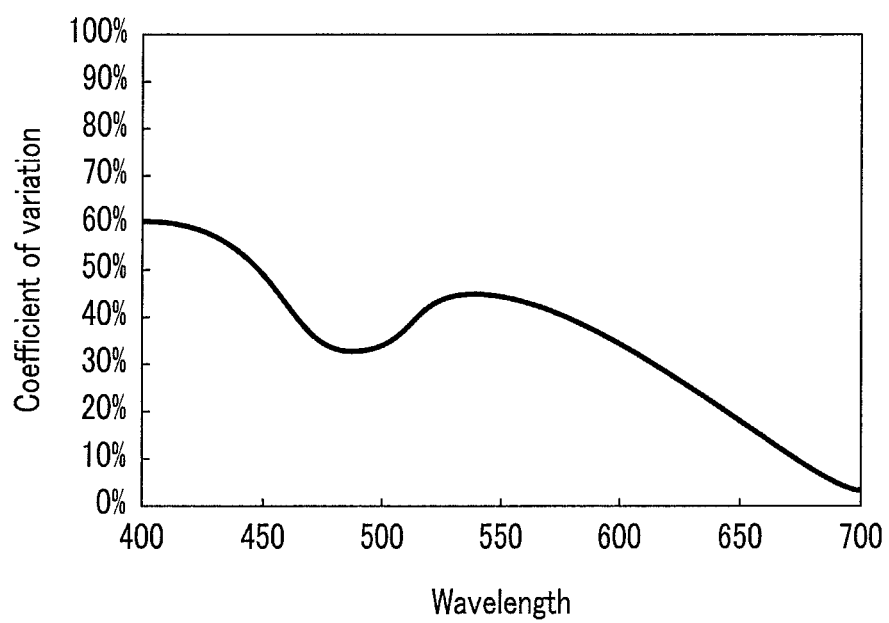
FIG. 9 is a graph showing an example of a coefficient of variation at the wavelength for each of the subjects of subject type numbers M1 to M10 and V1 to V10.

In the first embodiment, parameters of a coefficient of variation and a coefficient of relative variation are introduced in order to decide each narrow spectral light wavelength as a brightness index value and an assumed subject type index value. Here, the coefficient of variation is assumed as a value obtained by dividing a standard deviation for each wavelength of spectral reflectances for the assumed subject types by an arithmetic mean for each wavelength (percentage). FIG. 9 shows an example of the coefficient of variation at each wavelength. A value obtained by dividing the coefficient of variation at all wavelengths by the coefficient of variation at a wavelength of the highest coefficient of variation in a range from 380 to 780 nm of visible light is defined as a coefficient of relative variation (percentage). FIG. 10 shows an example of the coefficient of relative variation at each wavelength.

As for the brightness index value, since it has characteristics that do not rely upon the type of a subject O, such as the vascular area 78 and the mucosal area 76, but upon the distance and angle between the imaging element 42 and the subject O, a lower coefficient of variation is desirable to purely specify the brightness of the area of the subject O. It is desirable to use narrow-band light whose wavelength corresponds to a coefficient of relative variation of 20% or less when it is used. The reason is as follows: If the narrow-band light in the wavelength is used, the reflectance does not vary so much depending on the type of the subject O to obtain brightness information, which is derived from only the distance and angle of the subject O, with efficiency. According to FIG. 10, the coefficient of relative variation is 20% or less in the wavelength range of 660 nm or longer, and narrow-band light in the wavelength range of 660 nm or longer is desirable.

As for the assumed subject type index value, the type of the subject O such as the vascular area 78 and the mucosal area 76 should correctly be specified. Thus, a higher coefficient of relative variation is desirable and its numerical value purely reflects the type of the subject O. When the coefficient of variation is actually used, it is desirable to use narrow-band light whose wavelength corresponds to a coefficient of relative variation of 80% or more. The reason is as follows: If the narrow-band light in the wavelength is used, the reflectance varies greatly depending on the type of the subject O to specify the subject O correctly. According to FIG. 10, the coefficient of relative variation is 80% or less in the wavelength range from 400 nm to 450 nm, and narrow-band light in the wavelength range from 400 nm to 450 nm is desirable.

Since, however, the signal value acquired by the imaging element 42 is influenced by the distance and angle of the subject O even in a wavelength range whose coefficient of relative variation is high, it will be varied with a parameter that does not rely on the subject types. Thus, the signal value itself cannot be the assumed subject type index value but needs to be computed. Since the parameter that does not rely on the subject types can be extracted by the brightness index value, it is desirable to obtain a numerical value by dividing the spectral reflectance by the parameter as an assumed subject type index value to be actually used.

FIG. 11 shows relative spectral reflectance obtained by normalizing the assumed spectral reflectance of the assumed subject types shown in FIG. 6 by the reflectance at 660 nm that is a parameter not relying on the subject types (each spectral reflectance is divided by the reflectance at 660 nm). In FIG. 11, the subject type numbers V represent an example of spectra of the vascular area 78 existing in all organ ranges on the inner wall of internal organs of human beings, and the subject type numbers M represent an example of spectra of the mucosal area 76 existing in the same manner. Obviously, the vascular area 78 has a higher hemoglobin concentration and is very reddish.

Since, however, brightness greatly varies with the conditions other than the foregoing hemoglobin concentration, it is necessary to cancel a brightness variation due to the conditions. To do this, it is preferable to use, as an assumed subject type index value, the following equation (1) representing the ratio of the wavelength in a range from 400 to 450 nm to the wavelength in a range of 660 nm or longer, which can specify the brightness.

$$\text{laser light with a wavelength in a range from 400 to 450 nm/laser light with a wavelength in a range of 660 nm or longer} \quad (1)$$

In the first embodiment, blue-violet laser light with a wavelength of approximately 405 nm is adopted as narrow-band light whose wavelength corresponds to a coefficient of relative variation of 80% or more (first wavelength narrow-band light) and red laser light with a wavelength of approximately 660 nm is adopted as narrow-band light whose wavelength corresponds to a coefficient of relative variation of 20% or less (second wavelength narrow-band light). In the first embodiment, therefore, the following equation (2) is derived from the above equation (1).

$$\text{wavelength laser light with a wavelength of 405 nm/wavelength laser light with a wavelength of 660 nm} \quad (2)$$

This value is called a 405 nm/660 nm signal value as the "assumed subject type index value."

Then, the subject type storage 48 has stored a subject type number corresponding to each value of the 405 nm/660 nm signal value as a first data table, as shown in FIG. 12.

<Brightness Index Value Decision Circuit 50>

The brightness index value decision circuit 50 receives, from the imaging element 42, an acquired 660 nm image signal that is a second wavelength image signal and is distributed by the signal distribution circuit 44, and decides a brightness index value using a signal value of the received signal as a parameter.

As described above, for the endoscope apparatus 10 to observe a living body inner wall, the wavelength at which the brightness of an object can correctly be specified without relying on the type of the subject O is 660 nm or longer. The brightness index value decision circuit 50 thus receives an acquired 660 nm image signal value from the signal distribution circuit 44 and transmits it to the subject type decision circuit 46 and the display image decision circuit 52 as a brightness index value as it is.

Specifically, as described above with reference to FIG. 5A, the imaging element 42 includes pixels 72, and signal values of the pixels 72 are transmitted in sequence as acquired 660 nm image signal values. When the subject type decision circuit 46 and the display image decision circuit 52 decide an assumed subject type and a display image for each pixel, the brightness index value decision circuit 50 decides a brightness index value with a decision unit 74 of the brightness index value as 1×1 pixel size, as shown in FIG. 5A.

When the subject type decision circuit 46 and the display image decision circuit 52 have no other choice but to have a structure that is inferior in processing ability or processing speed, the brightness index value decision circuit 50 decides an assumed subject type and a display image for each group of pixels. For example, the brightness index value decision circuit 50 decides a brightness index value with the decision unit 74 of the brightness index value as 4×4 pixel size, as shown in FIG. 5B. In this case, however, while the acquired 660 nm image signal value, which is distributed by the signal distribution circuit 44 and transmitted from the imaging element 42, is stored temporarily in an internal memory (not shown), the signal values of the decision unit 74 of the brightness index value need to be averaged and the like to decide a brightness index value.

<Subject Type Decision Circuit 46>

The subject type decision circuit 46 fulfils a function of deciding a subject type number for each pixel or for each group of pixels using a numerical value obtained by computing the received 405 nm image signal and brightness index value as an assumed subject type index value for each pixel or for each group of pixels, and transmitting the information to the display image decision circuit 52.

More specifically, the subject type decision circuit 46 receives an acquired 405 nm image signal that is a first wavelength image signal from the imaging element 42 and is distributed by the signal distribution circuit 44, and stores it temporarily in the internal memory (not shown). Then, the subject type decision circuit 46 receives a brightness index value that is a parameter for each pixel or for each group of pixels, from the brightness index value decision circuit 50, and computes an assumed subject type index value. In other words, the subject type decision circuit 46 reads the acquired 405 nm image signal stored in the internal memory for each pixel and computes a 405 nm/660 nm signal value that is a ratio of the signal value of the read signal to the brightness index value. Alternatively, the subject type decision circuit 46 reads the acquired 405 nm image signals from the internal memory for each group of pixels, computes, for example, an average of the read signals for each group of pixels, and computes a 405 nm/660 nm signal value that is a ratio of the computed value to the brightness index value. Then, the subject type decision circuit 46 decides a subject type number for each pixel or for each group of pixels with reference to the first data table stored in the subject type storage 48 on the basis of the computed 405 nm/660 nm signal value.

<Display Image Decision Circuit 52>

The display image decision circuit 52 receives the subject type number for each pixel or for each group of pixels decided by the subject type decision circuit 46 and the brightness index value for each pixel or for each group of pixels decided by the brightness index value decision circuit 50 to decide a display image signal value for each pixel or for each group of pixels uniquely, referring to a second data table stored in the display image storage 54 based on these values, as will be described later. Then, the display image decision circuit 52 outputs the decided display image signal to the display 16. Accordingly, a display image with high color reproducibility for a specified subject O can be displayed on the display 16.

<Display Image Memory 54>

The display image storage 54 has stored a second data table representing display image signal values corresponding to the subject type numbers and the brightness index values, as shown in FIG. 13. In the first embodiment, the brightness index values are an integer of 0 or more because image signal values are adopted.

The display image decision circuit 52 can select a display image signal value, namely, a display color, referring to the second table in the display image storage 54, using the received subject type numbers and brightness index values as parameters.

Accordingly, a high color reproducibility image can be constructed even though illumination with quite low color rendering using a ray or rays of narrow-band light is applied.

In this case, detailed spectrum information as shown in FIG. 6 need not be stored in the display image storage 54, but a display color corresponding to a specified subject type number has only to be selected appropriately and stored.

A method of computing a display color with high color reproducibility to be stored in the display image storage 54 will be described below.

Since a brightness index value is correctly specified for each pixel, 660 nm spectral reflectance for the subject O in the target pixel is computed by dividing the spectral reflectance by the quantity of 660 nm laser light input to the target pixel.

Since a subject type is also specified for each pixel, a normalized spectral spectrum is known in advance. If, therefore, the normalized spectral spectrum is multiplied by the 660 nm spectral reflectance, spectral reflectance for the subject O in the target pixel is computed. If spectral reflectance for the subject O in the target pixel is known, an image signal can be acquired when high color rendering illumination is applied to the subject O by computing a premeasurable parameter such as an incident intensity spectrum of a standard light source that is high color rendering illumination and an imaging element spectral sensitivity spectrum. Detailed computation equations will be given below.

In the computation equations, the incident intensity spectrum of a standard light source in the target pixel is $e(\lambda)$, the imaging element spectral sensitivity spectrum is $s(\lambda)$, the color filter spectrum transmittances of the imaging element 42 for primary colors are $f_R(\lambda)$, $f_G(\lambda)$, and $f_B(\lambda)$, the 660 nm normalized spectral spectrum corresponding to a subject type number specified in the target pixel is $t(\lambda)$, the brightness index value is Y, the quantity of 660 nm incident light in the target pixel is $L_{660}$, and the coefficient caused by an imaging element photoelectric conversion rate, amplifier efficiency, etc. is a. In this definition, image signals $g_R$, $g_G$, and $g_B$ of the primary colors acquired when the standard light source is applied to the subject O that is currently observed, are each represented by the following equations (3).

$$g_R = a \frac{Y}{L_{660}} \int_{700\,nm}^{400\,nm} f_R(\lambda) s(\lambda) e(\lambda) t(\lambda)$$
$$g_G = a \frac{Y}{L_{660}} \int_{700\,nm}^{400\,nm} f_G(\lambda) s(\lambda) e(\lambda) t(\lambda)$$
$$g_B = a \frac{Y}{L_{660}} \int_{700\,nm}^{400\,nm} f_B(\lambda) s(\lambda) e(\lambda) t(\lambda)$$

(3)

As the above standard light source, a xenon light source, a halogen light source, a black-body radiation spectrum, solar light, an artificial solar light spectrum light source that imitates solar light and is provided by, e.g. the JIS, etc., which are high color rendering light sources, are particularly desirable.

Figure 14:
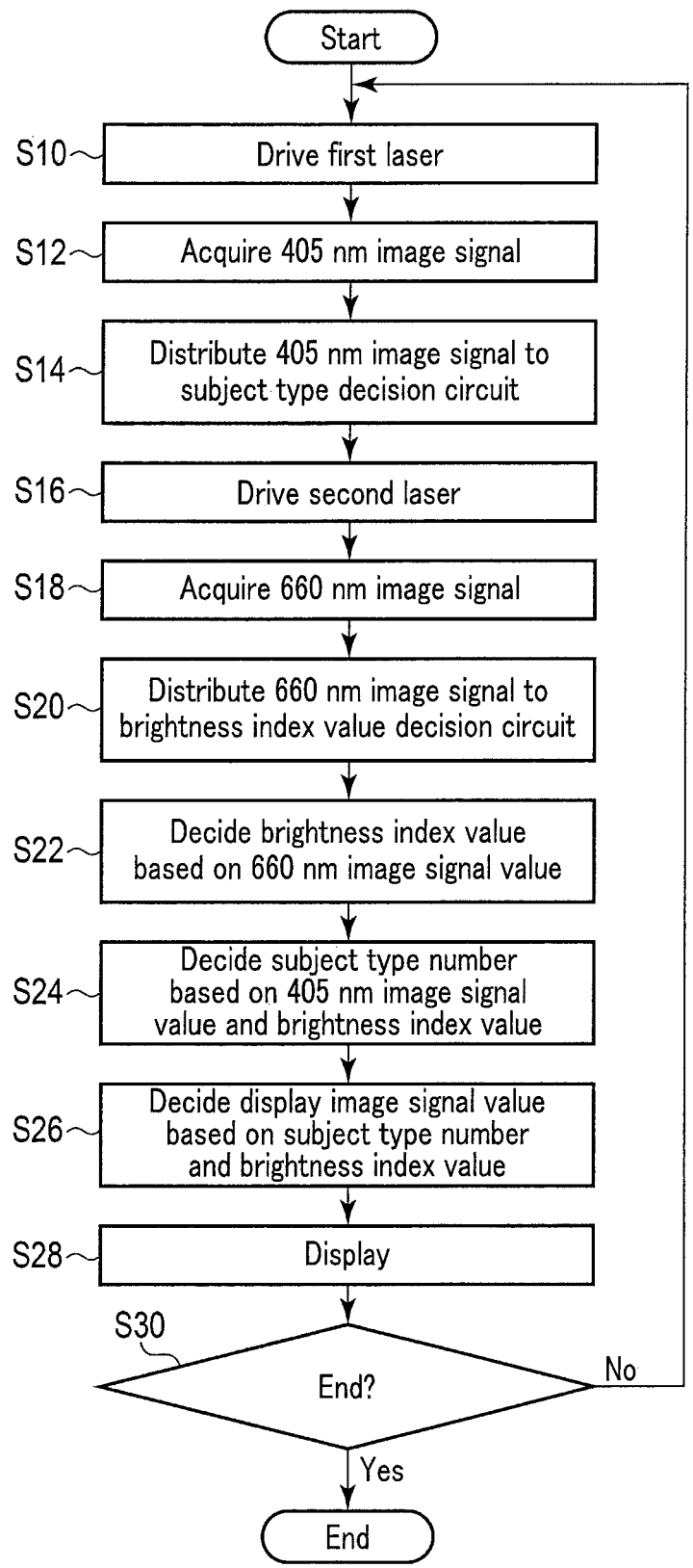
FIG. 14 is a flowchart showing an operation of the endoscope apparatus according to the first embodiment.

The operation of the endoscope apparatus 10 according to the first embodiment will be described further below with reference to the flowchart of FIG. 14. When an operator instructs the endoscope apparatus 10 to start to make an observation using an operating switch, etc. of an input device (not shown), the operation of the flowchart is started by a controller (not shown).

First, the light source controlling circuit 28 drives the first laser 24 to cause blue-violet laser light with a wavelength of approximately 405 nm (first wavelength narrow-band light) to be radiated from the distal end section of the insertion section 12 to the forward subject O as illumination light (step S10). Accordingly, the imaging element 42 that is an imaging device acquires a 405 nm image signal (first wavelength image signal) (step S12). Then, the signal distribution circuit 44 distributes the 405 nm image signal acquired by the imaging element 42 to the subject type decision circuit 46 to cause a 405 nm image signal value to be stored in the subject type decision circuit 46 (step S14).

Then, the light source controlling circuit 28 switches a laser to be driven from the first laser 24 to the second laser 26 to cause red laser light with a wavelength of approximately 660 nm (second wavelength narrow-band light) to be radiated from the distal end section of the insertion section 12 to the forward subject O as illumination light (step S16). Accordingly, the imaging element 42 that is an imaging device acquires a 660 nm image signal (second wavelength image signal) (step S18). Then, the signal distribution circuit 44 distributes the 660 nm image signal acquired by the imaging element 42 to the brightness index value decision circuit 50 (step S20).

The brightness index value decision circuit 50 decides a brightness index value using a value of the 660 nm image signal value acquired from the imaging element 42 through the signal distribution circuit 44, as a parameter, and transmits the decided brightness index value to the subject type decision circuit 46 and the display image decision circuit 52 (step S22).

The subject type decision circuit 46 decides a subject type number for each pixel or for each group of pixels, using the stored, acquired 405 nm image signal value and the brightness index value received from the brightness index value decision circuit 50 (step S24). That is, the subject type decision circuit 46 computes a 405 nm/660 nm signal value, which is the ratio of the acquired 405 nm image signal value to the brightness index value, for each pixel or for each group of pixels. Then, based on the 405 nm/660 nm signal value, the subject type decision circuit 46 decides a subject type number for each pixel or for each group of pixels, referring to the first data table stored in the subject type storage. The subject type decision circuit 46 transmits the subject type number so decided for each pixel or for each group of pixels, to the display image decision circuit 52.

The display image decision circuit 52 decides a display image signal value for each pixel or for each group of pixels, referring to the second data table stored in the display image storage 54, based on the subject type number decided by the subject type decision circuit 46 and the brightness index value decided by the brightness index value decision circuit 50 (step S26). Then, the display 16 displays a display image with high color reproducibility for a specified subject O in response to the display image signal from the display image decision circuit 52 (step S28).

After that, until the operator instructs the endoscope apparatus 10 to end the observation using the operating switch, etc. of an input device (not shown) (step S30), the operation from step S10 through step S28 is repeated by control of the controller (not shown).

As described above, the endoscope apparatus 10 according to the first embodiment includes the illumination apparatus 20 that applies illumination light to the subject O, the imaging element 42 that is an imaging device that acquires image light from the subject O with pixels to generate an acquisition image signal, and the image processing circuit 22 that constructs a display image signal based on the acquisition image signal, and particularly the illumination apparatus 20 radiates first wavelength narrow-band light and second wavelength narrow-band light that have peak wavelengths different from each other, and the image processing circuit 22 includes the subject type storage 48 that has stored assumed subject types that are assumed in advance as an observation target and the subject type decision circuit 46 that decides an assumed subject type for each pixel or for each group of pixels based on the first wavelength image signal acquired selectively as image light information regarding the first wavelength narrow-band light by the imaging element 42 in a state where at least the first wavelength narrow-band light is applied, the second wavelength image signal acquired selectively as image light information regarding the second wavelength narrow-band light by the imaging element 42 in a state where at least the second wavelength narrow-band light is applied, and the assumed subject types stored in the subject type storage 48.

Therefore, the endoscope apparatus 10 according to the first embodiment can specify a subject under observation, despite the use of a light source device using discrete narrow-band light, namely, low color rendering illumination light including the wavelength missing range 62.

The endoscope apparatus 10 according to the first embodiment further includes the brightness index value decision circuit 50 that decides a brightness index value from the second wavelength image signal and the display image decision circuit 52 that decides a display image signal based on the decided assumed subject type and brightness index value. A display image for observation is so decided based on the assumed subject type and the brightness index value, so that an image that matches the color of the assumed subject type can be acquired. In other words, despite the use of the light source device using discrete narrow-band light, namely, low color rendering illumination light including the wavelength missing range 62, color reproducibility of a display image for observation can be improved, and an image similar to the image acquired from the endoscope apparatus using a standard light source can be constructed. Particularly even in the endoscope apparatus 10 in which most of the ranges that can be detected by the imaging element 42 is the wavelength missing range 62, such as that laser light whose wavelength width is particularly narrow is used for illumination light as narrow-band light, an image that matches the actual biological color can be achieved.

Conventionally, a technology has been developed to estimate by a broad-spectrum illumination image an image formed when narrow spectrum light is applied, such that a specific portion is highlighted for an image signal acquired by broad spectrum illumination light from the standard light source (e.g. Jpn. Pat. Appln. KOKAI Publication No. 2011-194082). In contrast, in the endoscope apparatus 10 according to the first embodiment, a new technology is proposed in which narrow-band light such as laser light is used as illumination light to acquire correct spectrum subject information that is discrete in terms of wavelength and construct a high color reproducibility image based on the information.

As a common understanding among persons with ordinary skill in the art, when illumination light in use includes a wavelength missing portion, for example, a new LED has been added for the purpose of complementing the portion in order to construct a high color reproducibility image (e.g. Jpn. Pat. Appln. KOKAI Publication No. 2012-70839). In the endoscope apparatus 10 according to the first embodiment, however, a technology capable of constructing a high color reproducibility image using low color rendering illumination that generates no white light and most of which is the wavelength missing portion, is proposed.

Furthermore, in the endoscope apparatus 10 according to the first embodiment, the subject type storage 48 has stored the body of human beings or animals as assumed subject types that are assumed in advance as objects to be observed; thus, a high color reproducibility image can be constructed in the medical endoscope apparatus in which the body of human beings or animals is assumed as a subject O.

Furthermore, in the endoscope apparatus 10 according to the first embodiment, assuming spectral reflectances in which each spectral reflectance is the proportion of the quantity of light with each wavelength entering the imaging element 42 to the quantity of light applied to the assumed subject types, a coefficient of variation of the second wavelength regarding the assumed spectral reflectances is smaller than a coefficient of variation of the first wavelength regarding the assumed spectral reflectances. In other words, using an image signal generated when the second wavelength narrow-band light whose coefficient of relative variation regarding the assumed spectral reflectances is small is applied, the brightness of the area of the subject O can be specified regardless of the type for each area of the subject O; thus, a high color reproducibility image can be constructed.

Furthermore, in the endoscope apparatus 10 according to the first embodiment, the absorbance of the second wavelength for light-absorbing dye contained in an assumed subject type is smaller than that of the first wavelength.

In other words, using an image signal generated when second wavelength narrow-band light whose absorbance for light-absorbing dye contained in an assumed subject type is small is applied, the brightness of the area of the subject O can be specified regardless of the type for each area of the subject O; thus, a high color reproducibility image can be constructed. Moreover, when the second wavelength narrow-band light is applied to the subject O, it is reflected from the subject O with relatively high efficiency; thus, brightness can easily be recognized with a small quantity of light and information about brightness can correctly be obtained from a dark portion by decreasing driving power and adjusting quantity of light appropriately.

Moreover, in the endoscope apparatus 10 according to the first embodiment, the above second wavelength narrow-band light is narrow-band light with a wavelength at which the coefficient of relative variation is 20% or less when the coefficient of relative variation is 100% at a wavelength at which the coefficient of variation regarding the assumed spectral reflectances becomes the maximum. In other words, an image signal generated when narrow-band light with a short wavelength at which the coefficient of relative variation relative to the spectral reflectance of the subject O is 20% or less is applied is defined as a brightness index value. Since, therefore, the brightness of the area of the subject O can be specified regardless of the type for each area of the subject O, a high color reproducibility image can be constructed.

Moreover, in the endoscope apparatus 10 according to the first embodiment, using narrow-band light with a wavelength at which the coefficient of relative variation is 80% or more, as the first wavelength narrow-band light, the subject type decision circuit 46 selects an appropriate assumed subject type for each pixel or for each group of pixels from the assumed subject types stored in the subject type storage 48, based on the assumed subject type index value that is a computed value derived from the first wavelength image signal and the brightness index value. Since an image signal generated when narrow-band light with a long wavelength at which the coefficient of relative variation relative to the spectral reflectance of the subject O is 80% or more is applied is defined as a parameter used for the assumed subject type index value, an index that relies greatly upon the type for each area of the subject O can be obtained to specify a subject type and achieve a high color reproducibility image.

In the endoscope apparatus 10 according to the first embodiment, the computation using a brightness index value is a calculation divided by the brightness index value. In other words, since the ratio between image signal values obtained when light of wavelengths is applied is defined as an assumed subject type index value, the index value is an index from which a brightness component that is irrelevant to a subject color is eliminated, and a subject type is specified based on the index value. The subject type is therefore specified with high accuracy.

In the endoscope apparatus 10 according to the first embodiment, a subject includes hemoglobin as an absorbing dye, and the second wavelength narrow-band light is narrow-band light with a wavelength in a range of 660 nm or longer. Since an image signal acquired from the laser light with a wavelength in a range of 660 nm or longer that is hardly absorbed by hemoglobin is part of the assumed subject type index value, a brightness component that is irrelevant to the subject type is eliminated and thus the subject type is decided with high accuracy. Since, furthermore, an image signal acquired from laser light with a wavelength in a range of 660 nm or longer is defined as a brightness index value, a brightness index value that is hardly absorbed by hemoglobin that is the principal dye of the principal living body inner wall is obtained and thus brightness accuracy is high.

Furthermore, in the endoscope apparatus 10 according to the first embodiment, the first wavelength narrow-band light is narrow-band light with a wavelength in a range from 400 nm to 450 nm. Since an image signal acquired from the laser light with a wavelength in a range from 400 nm to 450 nm that is absorbed by hemoglobin with efficiency is part of the assumed subject type index value, a subtle color difference of the subject can be distinguished, and the subject type can be decided with high accuracy.

Furthermore, in the endoscope apparatus 10 according to the first embodiment, laser light is used as the narrow-band light. Since laser light that is narrow-band laser whose wavelength width is several nanometers or shorter is used, the spectral reflectance at a specific wavelength can be obtained with high accuracy, and the subject type can be correctly specified.

In the endoscope apparatus 10 according to the first embodiment, the display image decision circuit 52 decides a display image signal value for each pixel or for each group of pixels, referring to the second table stored in the display image storage 54, based on the subject type number and the brightness index value. Since the display image storage 54 includes a table capable of deciding a display image signal from the subject type number and the brightness index value, a display image can be decided quickly without placing a heavy load on the processor.

Furthermore, in the endoscope apparatus 10 according to the first embodiment, a xenon light source, a halogen light source, a black-body radiation spectrum, solar light, or an artificial solar light spectrum light source that imitates solar light is selected as the standard light source. It is thus possible to achieve high color reproducibility, despite the use of very low color rendering illumination.

Second Embodiment

A second embodiment of the present invention will be described below. In the description, reference will be made to how the second embodiment differs from the first embodiment. Therefore, the same symbols will be used to denote structural elements similar or corresponding to those of the first embodiment, and a description of such structural elements will be omitted.

As shown in FIG. 15, the endoscope apparatus 10 according to the second embodiment uses laser light with three wavelengths as illumination light to decide a brightness index value using an image signal acquired from laser light with a wavelength among the three wavelengths and decide a subject type using an image signal acquired from laser light with two wavelengths among the three wavelengths.

More specifically, the endoscope apparatus 10 according to the second embodiment includes a third laser 80 that emits third wavelength narrow-band light that differs in wavelength from the first wavelength narrow-band light and the second wavelength narrow-band light and an optical fiber 82 that guides the third wavelength narrow-band light to the combiner 30 from the third laser 80, in addition to the structural elements of the endoscope apparatus 10 according to the first embodiment. The combiner 30 is changed from the 2-in/1-out combiner of the first embodiment to a 3-in/1-out combiner.

The signal distribution circuit 44 is configured to transmit, to the subject type decision circuit 46, a third wavelength image signal acquired selectively by the imaging element 42 as image light information concerning the third wavelength narrow-band light while the third wavelength narrow-band light is applied.

The subject type storage 48 has stored a third data table representing the subject type numbers corresponding to first and second assumed subject type index values, in place of the first data table. The subject type decision circuit 46 computes first and second assumed subject type index values for each pixel or for each group of pixels based on first and third wavelength image signal values and a brightness index value to decide a subject type number for each pixel or for each group of pixels, referring to the third data table of the subject type storage 48, based on the first and second assumed subject type index values.

Note that the display image decision circuit 52 is basically similar to that of the first embodiment though the contents of the second data table increase because the number of assumed subjects increases, as will be described later.

For endoscope products in which a limited portion is observed, an assumed subject type is limited. Thus, two wavelengths may be enough for the laser wavelengths as in the first embodiment. However, for endoscope products in which a large portion and a variety of types are observed, the number of assumed subject types becomes large. To select one of them correctly, the number of rays of laser light should be added to maintain the subject type specification accuracy.

FIG. 16 shows spectral reflectance spectra of various subjects O when the number of assumed subject types increases. In this figure, residues (principal dye: bilirubin) remaining in the living body are newly added as an assumed subject type. In this figure, the subject type numbers M1 to M10 indicate a typical example of spectral reflectance spectra of a mucosal area, the subject type numbers V1 to V10 indicate a typical example of spectral reflectance spectra of a vascular area, and the subject type numbers S1 to S10 indicate a typical example of spectral reflectance spectra of a residue area. The subjects O are all photographed at the same subject distance and the same angle.

FIG. 17 shows an example of a coefficient of relative variation at each wavelength.

The endoscope apparatus 10 according to the second embodiment is also an endoscope apparatus designed to observe a living body inner wall as an observation target and thus the principal component in the subject O is hemoglobin. It is therefore desirable to select 405 nm and 660 nm as a wavelength, as in the first embodiment. In the second embodiment, however, it is difficult to specify a subject with these two wavelengths because a substance that is not mainly absorbed by hemoglobin is added to an assumed subject.

In the second embodiment, therefore, a second parameter is introduced.

Figure 18:
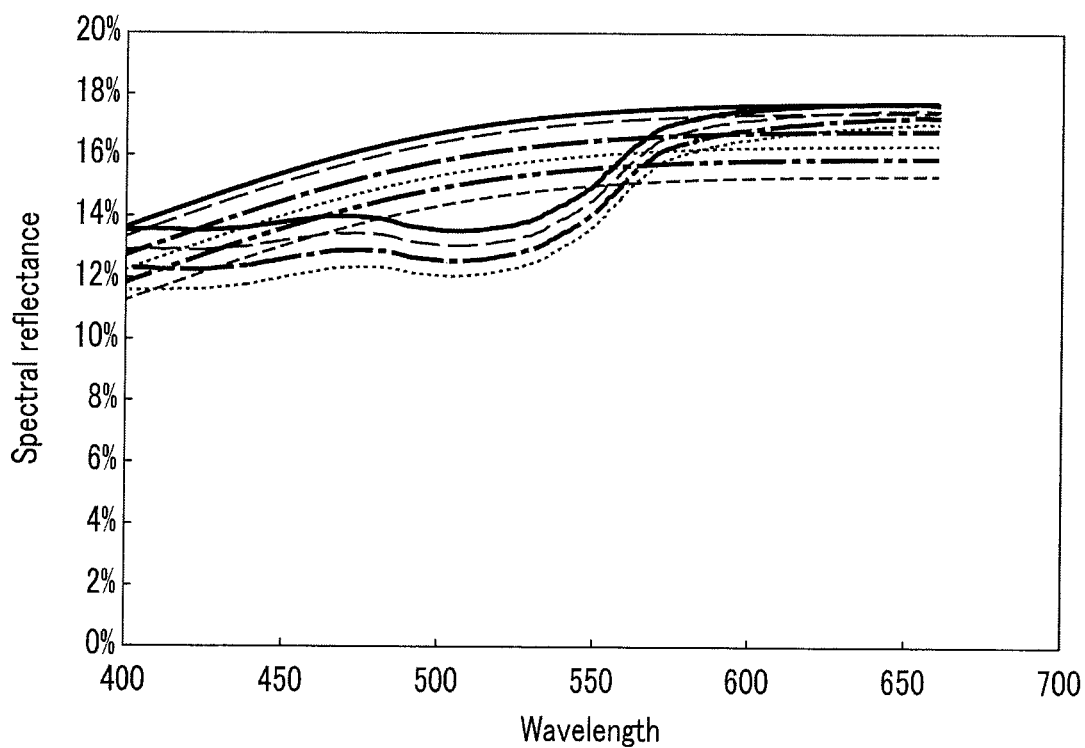
FIG. 18 is a graph illustrating a second assumed subject group.

First, as shown in FIG. 18, all spectra whose spectral reflectances at the second wavelength of 405 nm are almost the same are picked up. As shown in this figure, while bilirubin exhibits characteristics of absorbing light in a blue range sufficiently and transmits or reflects light in a green range and a red range, hemoglobin absorbs light in a blue range and a green range sufficiently.

Figure 19:
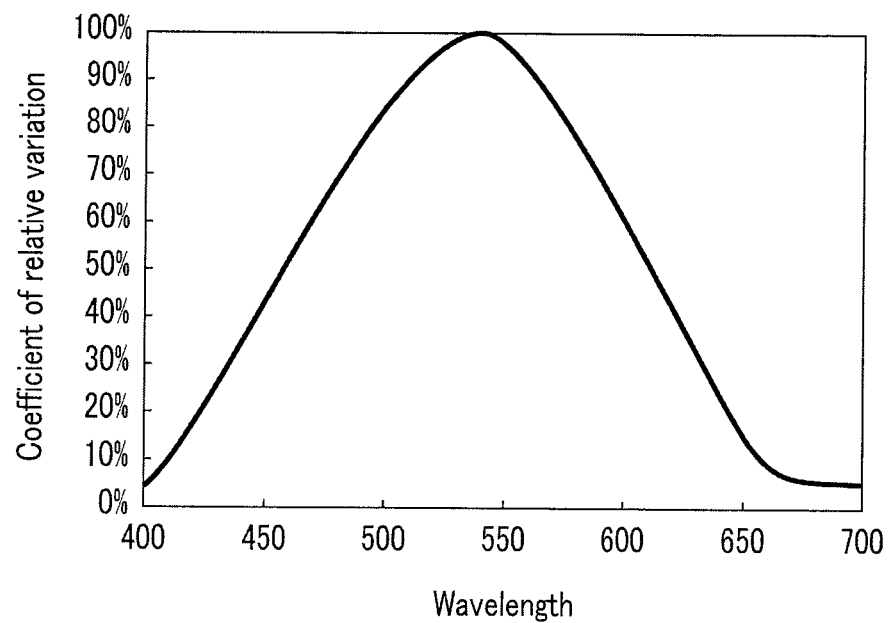
FIG. 19 is a graph showing an example of a coefficient of relative variation at each wavelength for the second assumed subject group.

FIG. 19 shows a coefficient of relative variation corresponding to the assumed subject spectral reflectance spectrum group (second assumed subject group) that are picked up. To specify a subject derived from bilirubin or a subject derived from hemoglobin, it is desirable that the coefficient of relative variation be 80% or more for the same reason as in the first embodiment and accordingly, it is desirable to set a wavelength range from 490 to 575 nm as is seen from FIG. 19.

In the second embodiment, therefore, the following two parameters of first and second assumed subject type index values are used as the assumed subject type index values.

Specifically, as the first assumed subject type index value of the first parameter, the following is desirable as in the first embodiment:

> laser light with a wavelength in a range from 400 to 450 nm/laser light with a wavelength in a range from 660 nm or longer and as the second assumed subject type index value of the second parameter, the following is desirable:

> laser light with a wavelength in a range from 490 to 575 nm/laser light with a wavelength in a range of 660 nm or longer (4)

In the second embodiment, laser light with a wavelength of 530 nm is used as the laser light in a range from 490 to 575 nm. In other words, as the third laser 80, a multimode semiconductor laser that emits green laser light with a wavelength of approximately 530 nm (third wavelength narrow-band light) is used. The subject type decision circuit 46 computes a 405 nm/660 nm signal value (first assumed subject type index value) and a 530 nm/660 nm signal value (second assumed subject type index value) as assumed subject type index values.

In the subject type storage 48 connected to the subject type decision circuit 46 through a signal line, subject type numbers, by which subject types are returned by inputting the specified 405 nm/660 nm signal value and 530 nm/660 nm signal value, are stored. In other words, as shown in FIG. 20, the third data table, which represents the subject type numbers corresponding to the 405 nm/660 nm signal value of the first assumed subject type index value and the 530 nm/660 nm signal value of the second assumed subject type index value, is stored in the subject type storage 48.

The subject type decision circuit 46 reads "subject type numbers" corresponding to the computed 405 nm/660 nm signal value and 530 nm/660 nm signal value from the third data table stored in the subject type storage 48 and transmits them to the display image decision circuit 52.

Note that in the third data table shown in FIG. 20, "E1" represents a subject that is not assumed or cannot be expected. In this case, there are two resolution methods.

The first resolution method is as follows: Since the area of a pixel or a group of pixels where the subject type number E1 is decided is assumed to be not a subject derived from the living body inner wall, it does not influence any observation directly without color reproducibility. Thus, with respect to the subject type number E1, a display image signal value indicating gray or black is set in the second data table of the display image storage 54, regardless of the brightness index value. The display image decision circuit 52 thus constructs a display image signal and causes the display 16 to display it uniformly in gray or black to make the area of the subject type number E1 inconspicuous.

The second resolution method is as follows: With respect to the subject type number E1, no display image signal value is set in the second data table of the display image storage 54, but the display image decision circuit 52 assigns a 405 nm image signal value, a 530 nm image signal value, and a 660 nm image signal value to a B channel of the display image signal, a G channel of the display image signal, and an R channel of the display image signal, respectively, and causes the display 16 to display them.

As described above, in the endoscope apparatus 10 according to the second embodiment, the subject type decision circuit 46 selects an appropriate assumed subject type, based on a second assumed subject type index value (second parameter) that is a computed value using a brightness index value, from an acquired third wavelength image signal in which image light information regarding third wavelength narrow-band light that differs in wavelength from first and second wavelength narrow-band light is selectively acquired, in addition to a first assumed subject type index value (first parameter). Assuming a second assumed subject group of assumed subjects having almost the same value as the first parameter, and assuming that a second coefficient of relative variation is 100% at a wavelength at which a coefficient of variation relative to a value of assumed spectral reflectance of the second assumed subject group becomes the maximum, the third wavelength narrow-band light is narrow-band light with a wavelength at which a second coefficient of relative variation is 80% or more.

Therefore, in the endoscope apparatus 10 according to the second embodiment, to assumed subject types having almost the same value in the first parameter, narrow-band light whose wavelength corresponds to a high coefficient of relative variation of 80% or more is used as the second parameter to the assumed subject types that are picked up, so as to specify an assumed subject type by two different indices. It is thus possible to specify the assumed subject type more correctly and obtain a high color reproducibility image. In other words, a high color reproducibility image can be constructed even though illumination with quite low color rendering using a single narrow-band light or narrow-band light is applied.

Moreover, in the endoscope apparatus 10 according to the second embodiment, when the subject type decision circuit 46 fails to decide an assumed subject type, the display image decision circuit 52 decides to display an area corresponding to a display image signal in black or gray. Since, therefore, a pixel that does not correspond to a prestored assumed subject type is displayed in black or gray, a pixel that cannot be assumed is displayed in inconspicuous color and its influence on observation is reduced.

Alternatively, in the endoscope apparatus 10 according to the second embodiment, when the subject type decision circuit 46 fails to decide an assumed subject type, the display image decision circuit 52 assigns an image signal about narrow-band light whose wavelength is closest to 450 nm, included in the first to third wavelength narrow-band light, to a blue-color channel in the display image signal, assigns an image signal about narrow-band light whose wavelength is closest to 550 nm, included therein, to a green-color channel in the display image signal, and assigns an image signal about narrow-band light whose wavelength is closest to 650 nm, included therein, to a red-color channel in the display image signal. Since an image signal about narrow-band light whose wavelength is closest to 450 nm is assigned to the blue-color channel in the display image signal, an image signal about narrow-band light whose wavelength is closest to 550 nm is assigned to the green-color channel in the display image signal, and an image signal about narrow-band light whose wavelength is closest to 650 nm is assigned to the red-color channel in the display image signal, with respect to the pixel that does not correspond to a prestored assumed subject type, a pixel that cannot be assumed can be displayed in not high rendering color but color close to the original color, and the influence on observation can be reduced.

The present invention based on the embodiments has been described so far. The present invention is not limited to the foregoing embodiments, but various modifications and applications can be applied without departing from the spirit of the present invention.

For example, in the foregoing first and second embodiments, an example of a multimode semiconductor laser is only presented as a light source that emits narrow-band light, but the present invention is not limited to this example. Various lasers, such as a solid-state laser, a gas laser, a compound semiconductor laser combined with an SHG element, and the like, can be used. An S laser (superluminescent diode), an LED, etc. can also be used. A light source including a wavelength missing range 62, in which an LED and a laser are combined with a phosphor, is favorable.

If a single-mode laser is used, a subject type and a brightness index value are decided with high precision because the peak wavelength of narrow-band light is stabilized. If a multimode laser is used, it is effective in illuminating a large space because it can emit high-intensity narrow-band light.

When the narrow-band light is defined in this specification, the spectrum width of the light source is a full width at half maximum (FWHM) and 50 nm or less.

Furthermore, in the first and second embodiments, the monochrome imaging element 42 is used, but the present invention is not limited thereto. A color imaging element provided with a color filter can also be used to emit narrow-band light of two wavelengths at the same time and acquire image signals of the narrow-band light with pixels of different color types.

Furthermore, the signal distribution circuit 44 may transmit 660 nm image information to the subject type decision circuit 46. Instead, the transmission of a brightness index value to the subject type decision circuit 46 from the brightness index value decision circuit 50 is omitted. In this case, as hardware configuration of the signal distribution circuit 44, the signal line from the imaging element 42 is branched into two lines, one of the two lines is connected to a signal line to the subject type decision circuit 46, and the other is connected to a signal line to the brightness index value decision circuit 50 through a switch that is turned on in synchronization with the driving of the second laser 26 by the light source controlling circuit 28. The subject type decision circuit 46 has only to include an internal memory that stores image signals acquired from the imaging element 42 through the signal distribution circuit 44, in synchronization with the driving of the first and second lasers 24 and 26 in the first embodiment or the driving of the first, second and third lasers 24, 26, and 80 in the second embodiment, by the light source controlling circuit 28.

In addition, various modifications and applications can be made.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus comprising:
   an illumination apparatus configured to apply first wavelength narrow-band light and second wavelength narrow-band light that have peak wavelengths different from each other to a subject;
   an imaging device comprising pixels configured to acquire image light from the subject to generate an acquisition image signal; and
   an image processing circuit configured to:
   acquire:
      a first wavelength image signal that is image light information about the first wavelength narrow-band light; and
      a second wavelength image signal that is image light information about the second wavelength narrow-band light, the first and second wavelength image signals being included in the acquisition image signal;
   decide a brightness index value based on the second wavelength image signal;
   decide an assumed subject type for part of the pixels based on the first wavelength image signal and the brightness index value;
   access information on display colors, each of the display colors corresponding to one of assumed subject types and one of brightness index values; and
   construct a display image signal indicating a display color for the part of the pixels based on the accessed information on display colors, the display color indicated by the display image signal corresponding to the assumed subject type decided amongst the assumed subject types and the brightness index value decided amongst the brightness index values, wherein assuming spectral reflectances in which each spectral reflectance is a proportion of quantity of light with each wavelength entering the imaging device to quantity of light applied to the assumed subject types and assuming that a coefficient of relative variation is 100% at a wavelength at which a coefficient of variation regarding the assumed spectral reflectances becomes maximum, the first wavelength narrow-band light is narrow-band light with a wavelength at which the coefficient of relative variation is 80% or more, and wherein the image processing circuit is configured to decide the assumed subject type for the part of the pixels from the assumed subject types, based on a first assumed subject type index value that is a computed value derived from the first wavelength image signal and the brightness index value.

2. The endoscope apparatus according to claim 1, wherein, assuming spectral reflectances in which each spectral reflectance is a proportion of quantity of light with each wavelength entering the imaging device to quantity of light applied to the assumed subject types, a coefficient of variation of the second wavelength regarding the assumed spectral reflectances is smaller than a coefficient of variation of the first wavelength regarding the assumed spectral reflectances.

3. The endoscope apparatus according to claim 2, wherein, assuming that a coefficient of relative variation is 100% at a wavelength at which a coefficient of variation regarding the assumed spectral reflectances becomes the maximum, the second wavelength narrow-band light is narrow-band light with a wavelength at which the coefficient of relative variation is 20% or less.

4. The endoscope apparatus according to claim 1, wherein absorbance of the second wavelength narrow-band light for light-absorbing dye contained in the assumed subject type is smaller than absorbance of the first wavelength narrow-band light.

5. The endoscope apparatus according to claim 1, wherein:

the image processing circuit is configured to decide the assumed subject type, based on a second assumed subject type index value that is a computed value using the brightness index value, from an acquired third wavelength image signal in which image light information regarding third wavelength narrow-band light that differs in wavelength from the first and second wavelength narrow-band light is selectively acquired, in addition to the first assumed subject type index value; and assuming a second assumed subject group that includes assumed subject types having almost a same value as the first assumed subject type index value and assuming that a second coefficient of relative variation is 100% at a wavelength at which a coefficient of variation relative to a value of the assumed spectral reflectance of the second assumed subject group becomes maximum, the third wavelength narrow-band light is narrow-band light with a wavelength at which a second coefficient of relative variation is 80% or more.

6. The endoscope apparatus according to claim 5, wherein computation using the brightness index value is a calculation divided by the brightness index value.

7. The endoscope apparatus according to claim 5, wherein when the image processing circuit fails to decide the assumed subject type, the image processing circuit is configured to decide to display a corresponding part in the display image signal in black or gray.

8. The endoscope apparatus according to claim 6, wherein when the image processing circuit fails to decide the assumed subject type, the image processing circuit is configured to assign an image signal about narrow-band light whose wavelength is closest to 450 nm, included in the first to third wavelength narrow-band light, to a blue-color channel in the display image signal, assign an image signal about narrow-band light whose wavelength is closest to 550 nm, included therein, to a green-color channel in the display image signal, and assign an image signal about narrow-band light whose wavelength is closest to 650 nm, included therein, to a red-color channel in the display image signal.

9. The endoscope apparatus according to claim 8, wherein:

the subject includes hemoglobin as an absorbing dye; and the second wavelength narrow-band light is narrow-band light with a wavelength in a range of 660 nm or longer.

10. The endoscope apparatus according to claim 9, wherein the first wavelength narrow-band light is narrow-band light with a wavelength in a range from 400 nm to 450 nm.

11. The endoscope apparatus according to claim 1, wherein each of the first wavelength narrow-band light and the second wavelength narrow-band light is laser light.

12. The endoscope apparatus according to claim 1, wherein the assumed subject types include information about a wavelength range of assumed subjects.

\* \* \* \* \*